United States Patent [19]

Mabie et al.

[11] 4,217,264
[45] Aug. 12, 1980

[54] MICROPOROUS GLASSY FILLERS FOR DENTAL RESIN COMPOSITES

[75] Inventors: Curtis P. Mabie, Thurmont; Daniel L. Menis, Gaithersburg, both of Md.

[73] Assignee: American Dental Association Health Foundation, Washington, D.C.

[21] Appl. No.: 941,308

[22] Filed: Sep. 11, 1978

Related U.S. Application Data

[63] Continuation-in-part of Ser. No. 783,760, Apr. 1, 1977, abandoned.

[51] Int. Cl.² .......................... A61K 5/06; C08K 3/36; C08W 33/12
[52] U.S. Cl. ............................. 260/42.15; 433/228; 106/35; 106/40 V; 106/40 R; 106/52; 106/288 B; 106/299; 428/376; 260/998.11; 428/404
[58] Field of Search ............. 260/998.11, 42.15, 42.14; 106/35, 52, 299, 288 B, 40 V, 40 R; 32/15; 428/404

[56] References Cited

U.S. PATENT DOCUMENTS

| | | | |
|---|---|---|---|
| 3,597,252 | 8/1971 | Schroeder et al. | 106/52 |
| 3,759,683 | 9/1973 | Dislieh et al. | 106/52 |
| 3,926,906 | 12/1975 | Lee et al. | 260/42.15 X |
| 3,936,887 | 2/1976 | Hodosh | 260/998.11 |
| 3,971,754 | 7/1976 | Jurecic | 32/15 |
| 3,974,104 | 8/1976 | Foster et al. | 106/35 X |
| 4,021,253 | 5/1977 | Budrick et al. | 106/52 X |
| 4,059,658 | 11/1977 | Shoup et al. | 106/35 X |
| 4,065,317 | 12/1977 | Baak et al. | 106/52 |
| 4,143,018 | 3/1979 | Crisp et al. | 260/998.11 |
| 4,150,012 | 4/1979 | Joos | 260/42.15 |
| 4,157,907 | 6/1979 | Kroyer | 428/404 X |

FOREIGN PATENT DOCUMENTS

1963552 8/1970 Fed. Rep. of Germany ...... 260/998.11
992782 5/1965 United Kingdom .

OTHER PUBLICATIONS

Mabie, C. P. et al., "Microporous Glassy Fillers for Dental Composites", J. Biomed. Mats. Res. 12 (1978) pp. 435–472.
Mukherjee, S. P. et al., "A Comparative Study of Gels and Oxide Mixtures as Starting Materials for the Nucleation and Crystallization of Silicate Glasses", J. of Mat. Sci., 11 (1976) pp. 341–355. .
Bowen, R. L., "Semiporous Reinforcing Fillers for Composite Resins", J. of Dental Res., vol. 55 (Feb. 1, 1976) (Special Issue B) p. B 139, Abstr. 310.
Bowen, R. L., "Semiporous Reinforcing Fillers for Composite Resins: I Preparation of Provisional Glass Formulations, " and Oct. 1976, Idem. II, Heat Treatments and Etching Characteristic, J. Dental Research, vol. 55 (5) pp. 738–756 (Sep.–Oct. 1976).
McCarthy, G. J. et al., "Gel Route to Homogeneous Glass Preparation II, Gelling and Desiccation", J. Am. Cer. Soc. –Dec. 1971–pp. 639–640.

Primary Examiner—Helen M. McCarthy
Attorney, Agent, or Firm—Allegretti, Newitt, Witcoff & McAndrews

[57] ABSTRACT

A microporous filler for dental composite resin restorations has been developed which gives greatly improved finishability, system non-toxicity and x-ray opacification. These fillers are prepared from frits obtained by the low temperature calcination of gelled inorganic "polymers" followed by a pulsed high-heat treatment.

15 Claims, 6 Drawing Figures

MICROPOROUS GLASSY FILLERS FOR DENTAL RESIN COMPOSITES

The invention described herein was made in the course of work under a grant or award from the Department of Health, Education and Welfare.

This is a continuation of application Ser. No. 783,760, filed Apr. 1, 1977, now abandoned.

BACKGROUND OF THE INVENTION

Dental cements have been undergoing continuous developments since before the use of powdered zinc oxide mixed with eugenol about a century ago. The important characteristics which a dental composite must exhibit include: adequate mechanical properties such as strength, hardness, smoothness and abrasion resistance; optical characteristics that permit a simulation of the tooth such as color matching, color stability and a matching index of refraction; and a variety of more complex characteristics which assure compatability with the human body in an oral environment such as non-toxicity, non-solubility, low water absorption and radiopacity to name a few.

Early successful composite resin dental restorations for anterior implacement were prepared by Bowen in 1963. He used a silane-coated fused quartz powder as filler. In 1969 Chang recommended the use of fillers approximating the refractive index of the resin matrix consisting of glass beads and subordinate amounts of glass fibers and lithium aluminum silicate powder. Chang states that glass beads used as filler can range anywhere from 5 to 100 microns in diameter. Lithium aluminum silicate powder is used by Chang as a fine-grained component and contains both spodumene and $\beta$ eucryptite to give low thermal expansion characteristics to the composite. See Bowen, Properties of a Silica-reinforced Polymer for Dental Restorations, 66 J ADA 57–64 (Jan. 1963); CHANG, U.S. Pat. No. 3,452,437.

LEE II, U.S. Pat. No. 3,539,533 states that aluminum oxide may be used as a filler but recognizes that its high refractive index ($>1.75$) gives unsatisfactory translucency for anterior restorations. He found that mixtures of quartz and glass beads are satisfactory esthetically as fillers. His contention is that the quartz must be ground through 200 mesh U.S. sieves.

In the patents of both CHANG and LEE II, and in all subsequent patents surveyed, the filler is given a silane coating. Commonly the silane is carried on to the filler with aqueous solutions; e.g. LEE II uses dilute acetic acid silane solutions.

WALLER, U.S. Pat. No. 3,629,187 recommends the use of both ceramic and glass fillers less than 25 microns in diameter. He claims that the use of mixtures of ceramic and glass fillers allows for the preparation of a good particle-size distribution in the filler fraction so that the composite product may contain both fines and particles nearing the maximum diameter of 25 microns. In WALLER, the glasses that can be used may be phosphate or silica. The ceramic filler that he particularly recommends using is lithium aluminum silicate powder with a view to lowering the thermal expansion and is probably a major component of the fines.

GANDER, U.S. Pat. No. 3,835,090 states that representative fillers utilized for restorative resin composites are quartz, glass beads, aluminum oxide, and fused quartz, or silica. The inventor states that a preferable size range is 25–30 $\mu$m. Mica, glass fiber, and nylon filled plastic composites have been evaluated by others.

As a further improvement in the fillers used in restorative resin composites, ROSSI, U.S. Pat. No. 3,792,531 discloses filler systems which are stated to give improved polishability (finishability). These filler systems utilize fine crystalline quartz with diameters between 0.70 and 30 $\mu$m. Eighty percent of the quartz particles by weight are to be less than 20 $\mu$m in diameter and 20 percent less than 5 $\mu$m in diameter. ROSSI states that larger particles are loosely held by the resin and therefore are susceptible to being gouged out by routine polishing techniques.

Filler materials having low thermal expansions have been recommended by BOYD, U.S. Pat. No. 3,503,128. That patent suggests topaz, $4.7 \times 10^{-6}/°C$.; alumina, $8.7 \times 10^{-6}/°C$.; zirconium orthosilicate (zircon), $4.2 \times 10^{-6}/°C$.; and white beryl, $-1.35 \times 10^{-6}/°C$. All, with the exception of white beryl, have refractive indices which are too high to yield anterior restorations having satisfactory translucencies. The lowest thermal expansion composites disclosed in that patent has an expansion of 19.1 to $27.9 \times 10^{-6}/°C$. over a temperature range 0° to 60° C. utilizing $\beta$ eucryptite in major amounts.

X-ray opacifying fillers were first introduced in glass form by Bowen and Cleek. See Bowen and Cleek, X-ray-Opaque Reinforcing Fillers For Composite Materials, 48 J Dental Research, No. 1 (Jan-Feb 1969). These glasses contained 24 to 28 mole percent of barium fluoride plus oxide. A glass composition which was considered particularly favorable contained in mole percent $SiO_2$, 44; $BaF_2$, 28; $B_2O_3$, 16; and $Al_2O_3$, 12; or in weight percent, $SiO_2$, 26.72; $BaF_2$, 49.64; $B_2O_3$, 11.27; and $Al_2O_3$, 12.37.

Another set of radiopacifying glass was later developed by Bowen and Cleek. See Bowen and Cleek, A New Series of X-ray-Opaque Reinforcing Fillers for Composite Materials, 51 J Dental Research, No. 1 (Jan-Feb 1972). They could not obtain glasses with refractive indices less than 1.592 which contained more than 7 mole percent $ZrO_2$. Also, these glasses were heterogeneous and had only 7 mole percent of BaO. In weight percent these maximum zirconium-containing glasses had $ZrO_2$, 11.7, and BaO, 14.5. In their later glasses a particularly favorable composition contained in mole percent $SiO_2$, 66; BaO, 17; $B_2O_3$, 6; $Al_2O_3$, 11; or in weight percent, $SiO_2$, 49.87; BaO, 32.80; $B_2O_3$, 9.64; and $Al_2O_3$, 7.69.

CHANDLER was the first to apply and evaluate Bowen's radiopaque glass-resin composites. See Chandler, Bowen and Paffenbarger, Clinical Evaluation of a Radiopaque Composite Restorative Material After Three and a Half Years, 52 J Dental Research, 1128–1137, No. 5 (1973). Anterior restorations were prepared utilizing approximately 33 wt% of a Corning $BaF_2$ glass and 66.7 wt% of a Corning fused silica in the filler fraction.

Later DIETZ, U.S. Pat. No. 3,826,778 suggested barium aluminum silicate glasses which contain greater than 22.5 wt% BaO. It stated that the optimum radiopacifying glass consists of the following weight percentages: $SiO_2$, 25–35; $Al_2O_3$, 10–20; and BaO, 50–60.

MULLER has developed $La_2O_3$ containing glass-ceramics with a high radiopacifying powder. See Muller, Glass Ceramics as Composite Fillers, 53 J Dental Research, 1342–1345, No. 6 (Nov-Dec 1974). These contain up to 15 wt% $La_2O_3$. However, the Vicker's microhardness of these fillers is high, 950 kg/mm$^2$, and is probably objectionable in finishing.

A few of the many additional patents and printed publications which investigate metal oxides, silica, quartz, mica, ground glass, and other materials for use as fillers in dental composites include: Muller, U.S. Pat. No. 3,973,972; Mabie, U.S. Pat. No. 3,973,970; Jurecic, U.S. Pat. No. 3,971,754; Dietz, U.S. Pat. No. 3,801,344; Overhults, U.S. Pat. No. 3,839,065; Wilson et al, U.S. Pat. No. 3,814,717; Brigham, U.S. Pat. No. 3,649,732; Siegel, U.S. Pat. No. 3,504,437; and Saffir, U.S. Pat. No. 3,069,773.

Fillers made according to the prior art have many disadvantages which it is the object of this invention to overcome. Glass beads have been observed commonly to be subject to extensive plucking out on finishing. Quartz fillers, except when extremely fine, degrade under impact finishing or else remain high above the resin matrix when the finishing becomes worn.

Typical quartz and glass bead fillers give very rough finishes. A better finish using quartz-filled composites may be obtained only if the particle size of the quartz filler is reduced to a point where it raises the BIS-GMA paste viscosity excessively. This reduces the amount of filler than can be introduced into any give resin system.

Fillers using fused silica, spherical glass, quartz, ceramic and alumina generally do not have sufficient X-ray opacification or radiopacity to permit ready determination of decay under the composite restoration.

In order to delineate the composite restorations against both dentin and enamel, x-ray opaque materials were developed, but these glasses commonly contained considerable amounts of potentially soluble and possibly toxic constituents, e.g. BaF and BaO which can have an adverse effect on the nervous system. Furthermore, barium containing glass beads tend to severly degrade under the impact of finishing wheels.

Fillers having adequate radiopacity can be prepared using strontium, but the large mole percentage of strontium required will probably result in high solubility. Glass ceramics using $La_2O_3$ as an x-ray opacifier have also been investigated.

Some attempts to improve the finish of composites have focused on reducing the plucking of glass filler by etching the surface. Still other attempts have improved finish by using finer grained quartz.

In order to meet the objections of possible soluble toxic constituents and to improve finish and x-ray opacity, the microporous glass fillers of this invention have been developed. Improved finish is due, at least in part, to filler absorption of the impact of dental finishing wheels. Therefore, shock is not transmitted to the filler-grain resin interface. Also, these glasses give systemically non-toxic x-ray opacification.

BRIEF SUMMARY OF THE INVENTION

In general, the primary purpose of the newly developed filler product is to increase the finishability of dental composite resins and to provide a non-toxic, low solubility filler material which exhibits intense radio-opacification. These new filler products consist of frit grains prepared by a gel route. In addition to the above mentioned properties the restorative resin composites which have been prepared utilizing these frits as fillers also have a low thermal expansion, satisfactory strength, setting contraction, and optical translucency. These frit fillers may also be made to carry pigments, particularly carbon black, inside the filler grain so that they do not react with the resin, reduce shelf life or otherwise contribute to color instability.

The microporous glassy fillers of the present invention are prepared from a refractory inorganic oxide sol. This is a marked contrast to the prior art method of manufacturing glass fillers by a melt technique. The refractory inorganic oxide materials which can be used in accordance with the present invention include any refractory inorganic oxide material which is suitable for use in a dental filler environment. Preferred refractory inorganic oxide materials include silica and alumina.

According to the present invention, the filler material is a microporous glassy filler prepared from a gelled calcined refractory inorganic oxide sol. This material is then used as a replacement for at least a portion, if not all, of the filler materials conventionally used by the prior art in the preparation of a dental resin composite while the amount of filler in the resin composite can vary within wide limits, preferred are resin composites containing about 30 to about 90% by volume filler, and preferably about 40 to about 80% by volume filler.

As indicated, the filler material comprises a gelled calcined refractory inorganic oxide sol. According to the present invention, this material is prepared by first preparing a refractory inorganic oxide sol, gelling said sol at conditions sufficient to provide a gelled sol and then calcining the resultant gel to provide said microporous glassy filler.

Preparation of the sol may also include the addition of small amounts (less than 0.2 weight % as oxide) of a fluxing agent such as boric acid, sodium carbonate, lithium carbonate and mono-ammonium phosphate and a peptizing agent such as acetic acid. The fluxing agent aids in promoting densification. The peptizing agent aids in preparing the sol.

A dental resin composite can be made by mixing a dental resin with the filler material of this invention. The resin may comprise any resin system commonly used in the industry. The resin system may also call for the addition of small amounts of catalysts and stabilizers.

The filler material of this invention will comprise about 5 to about 95 percent by weight silicon dioxide, about 5 to about 95 percent by weight aluminum oxide, and about 3 to about 50 percent by weight of an x-ray opacifying compound. While any x-ray opacifying agent can be used, the preferred opacifying agents, because of their system nontoxicity are selected from the group consisting of zirconium, hafnium, tantalum or tin compounds. A preferred embodiment of the filler material of this invention comprises about 27 to about 57 percent by weight silicon dioxide, about 13 to about 60 percent by weight aluminum oxide and about 10 to about 36 percent by weight of an x-ray opacifying compound. Fillers made according to this invention using zirconium exclusively as the x-ray opacifying agent have contained zirconium at about 18 to about 36 percent of the filler compound in preferred form. Hafnium is a chemical twin of zirconium for purposes of this invention, except that hafnium has greater x-ray opacification capacities than zirconium, therefore requiring less hafnium than zirconium to produce equal x-ray opacity. Tin may also be used for this purpose.

The microporous glass filler made according to this invention may contain higher percentages of zirconium, hafnium and tin than conventional glass fillers made according to other methods without resulting in crystallization of the glass and devitrification of the glass during production.

Unlike conventional fillers, fillers made according to this invention may carry coloring pigments, such as carbon black, into the paste composite resin. The pigment does not degrade during production of the microporous glass as it would tend to do during production of a conventional glass filler. The pigment will not adversely react with the resin system because it will be contained within the core of the microporous glass frit. Thus, potentially deleterious pigments are insulated from chemically interacting with resin constituents.

For a frit of a given composition prepared according to this invention the refractive index is directly related to the density, i.e., the greater the density, the greater the refractive index. Microporosity, and therefore frit density, can be adjusted by heat treatment. At the high calcination temperatures, pulsed heat treatment can collapse micropores without excessive crystallization. It should be noted, however, regions of crystallization and crystallite formation may be excessively extensive. If so, the frits will have undesirable optical properties, in particular excessive optical opacification.

For a frit prepared according to a given procedure, the refractive index will also be directly related to the concentration of x-ray opacifying ingredients, i.e., the greater the concentration of zirconium, hafnium, tin or tantalum oxides, the greater the refractive index.

Translucency and other optical properties are partially dependent on the refractive index of the frit. For example, translucency is related to the difference between the refractive index of the frit and of the resin; the greater the difference between these refractive indexes, the greater will be opacity of the resulting product. Thus, translucency and many other optical properties of fillers prepared according to this invention can be adjusted either by the method of heat treating the gel or by the composition of the gel.

Microhardness can similarly be adjusted by modification of microporosity through heat treatment.

The low alkali and boric oxide content of gel-prepared frits, less than 0.2 wt%, indicate that these components will have low solubility in the oral environment. Other ingredients of the frits, $ZrO_2$, $HfO_2$, $SiO_2$ and $Al_2O_3$ are notably insoluble or only very sparsely soluble in water. This contrasts favorably with current barium-containing x-ray opaque glasses which contain in excess of 50 or 60 mass percent of potentially soluble barium oxide, barium fluoride, or boric oxides.

Frit preparation by the gel route and brief pulsating heat treatment yields glasses which cannot be obtained by conventional batch-melting procedures because of devitrification. Experimental composites prepared from the new fillers are within range of current products with regard to strength and setting time.

The products which have been produced utilizing frits prepared according to this invention are within the range of setting contraction, strength and thermal expansion generally expected of present, commercially available products. These gel products are superior in finishability. Even coarsely particulate gel-prepared frit fillers having 16.5 vol. % plus-200-mesh and only 50 vol. % minus-400-mesh material, exhibit little or no plucking. Quartz grain and glass fillers of other commercial products commonly have minute triangular pits formed by impact finishing. These pits will be extended in size and multiplied in number under finishing impact wear ultimately resulting in total loss of the filler grain.

The x-ray opacifying glass beads in still other commercial products, under scanning electron microscope (SEM) examination, exhibit degradation, shatter, and ultimately pluck out.

Textures resulting from filler removal occur as a continuous series. This textural evidence indicates that glass-filler degradation under impact causes most of the plucking.

SEM examinations of lightly and heavily finished experimental product restorations made according to this invention have demonstrated that these gel-prepared frit particles have mechanical compatibility with the resin. This frit filler does not show the impact degradation which is characteristic of current quartz grain and glass bead fillers.

The frit fillers prepared according to this invention have internal microporosity which promotes improved finish. The partial glass ceramic character of these frits also contributes to the improved finishing qualities. It is believed that absorption of the shock of dental finishing wheels is due to the peculiar structure of the grain, somewhat analogous to a porous vitreous grinding wheel.

Other objects and advantages of this invention include a filler which has a strengthening effect comparable to that of glass and other commercially available fillers. The diametrical tensile strength of 37° C. of prepared cylindrical specimens of our frit products and of one commercially available product, Adaptic filler for dental resin composites (hereinafter "Adaptic"), were generally comparable. Values of $332 \pm 23$ kg/c², were achieved for the frit product and $362 \pm 64$ kg/cm² for "Adaptic". Two-sided tests at 95% indicate that "Adaptic" is the same as this product in tensile strength. This close proximity in values of the new frit mix and "Adaptic" is particularly promising in light of the fact that the new frit product contains only 55.2 vol. % filler in the mixed paste vs. 61.0 vol. % filler for "Adaptic", i.e., 44.8 vs. 39.0 vol. % resin, respectively. Furthermore, many composites prepared from the novel frit fillers had equivalent flexural strength to "Adaptic".

The flexural strength of the products made with the novel frits was generally within a medium range of commercially available products. Comparison of the flexural strengths of good translucency frit products with no plus-200-mesh particles suggest that most strength deficiencies are associated with low filler content or prolonged setting times. Most frit containing products with room temperature setting times approximating that of "Adaptic," i.e., 2.5–3.5 min., would appear to be lower in flexural strength than "Adaptic" because of a lower filler content.

Improvement in strength was obtained with products having fluxed silica fiber addition to the filler fraction. Examination of the strengthening effects of fluxed silica fiber when blended with fused silica chips substantiates this conclusion.

Another favorable feature of the experimental frit fillers is their apparently low thermal expansion. A product with only 49.5 vol. % experimental frit as filler in the mixed paste has a linear coefficient of thermal expansion of $31.8 \times 10^{-6}$/°C. This value is essentially the same as "Adaptic" which has approximately 61 vol. % filler in the mixed paste and a linear thermal expansion coefficient of $32.0 \times 10^{-6}$/°C., $\pm 1 \times 10^{-6}$/°C. Another product with a filler content of 57.5 vol. % has a lower thermal expansion of $27.2 \times 10^{-6}$/°C.

Still another favorable feature of the experimental frit-containing products are the setting contractions which are equal to those of some commercial products and the thermal expansions which are equal to or better than commercial products. Slight increases in filler content may be expected to further reduce both setting contraction and thermal expansion considerably.

Design of frit particle size and shape parameters with regard to stereological considerations should be undertaken. Particles of the proper size and shape should be produced which optimize the number of contacts in three-dimensional networks which will result in products with minimal setting contraction and thermal expansion.

Stereological design should result in those particles with minimum degree of freedom for rotation. This is dependent upon the number of contacting particle pairs and the number of particle contacts between grain pairs. Thus, the most dimensionally stable system would be a three-dimensional network, hexagonally packed, with up to three contacts between each grain pair.

These and other objects, advantages and features of the invention will be set forth in the detailed description which follows.

BRIEF DESCRIPTION OF THE TABLES

In the detailed description which follows, reference will be made to TABLES I through XIX which set forth data concerning the fillers of the present invention, including test results performed to determine various characteristics of the various preferred embodiments of this invention.

TABLE I sets forth the composition of various resin mixes used testing preferred embodiments of the invention.

TABLE II sets forth the composition of various gelling mixtures used in testing preferred embodiments of the invention.

TABLE III sets forth the composition of various calcined frits used in testing preferred embodiments of the invention.

TABLE IV sets forth the calcination conditions of various frits used in testing preferred embodiments of the invention.

TABLE V sets forth data on the physical characteristics of various preferred embodiments of the invention.

TABLE VI sets forth data on comparable physical characteristics of currently available commercial fillers.

TABLE VII sets forth the relative composition of various mixes of currently available commercial fillers used in comparative testing with the preferred embodiments of this invention.

TABLE VIII sets forth the relative composition of various mixes of preferred embodiments of this invention and currently available commercial frits used in testing this invention.

TABLE IX sets forth the relative composition of paste, dental resin composites, prepared from the various resin and filler mixtures.

TABLE X sets forth data on setting contraction of some of the preferred embodiments of this invention and of currently available commercial fillers.

TABLE XI sets forth data on various physical characteristics of preferred embodiments of this invention, currently available commercial fillers, and various mixes of these fillers.

TABLE XII sets forth data on the thermal expansion under specified conditions of dental resin composites made from the specified fillers.

TABLE XIII sets forth data on the hardness of various dental resin composite specimens.

TABLE XIV sets forth data on the modulus of elasticity by compression of various dental resin composite specimens.

TABLE XV sets forth data on the diametrical tensile strength of various dental resin composite specimens.

TABLE XVI sets forth data on the flexural strength under specified conditions of various dental resin composite specimens.

TABLE XVII sets forth data on the water pickup of various dental resin composite specimens under certain conditions. The water pickup is measured in relation to the volume of the specimen.

TABLE XVIII also sets forth data on the water pickup of various dental resin composite specimens under certain conditions. The water pickup is measured in relation to the volume of solid paste of the specimen.

TABLE XIX sets forth data on the finishability of various dental resin composites made with various fillers according to this invention and otherwise currently available commercial fillers.

BRIEF DESCRIPTION OF THE DRAWINGS

In the detailed description which follows, reference will also be made to the following figures. The figures set forth data obtained from tests performed on preferred embodiments of the invention and pictures of the preferred embodiments of the invention under microscopic examination. Where a mix is referred to in the description of the following figures, reference is made to the mix compositions set forth in the tables identified above.

DETAILED DESCRIPTION OF THE PREFERRED EMBODIMENT OF THE INVENTION

Figure 1:
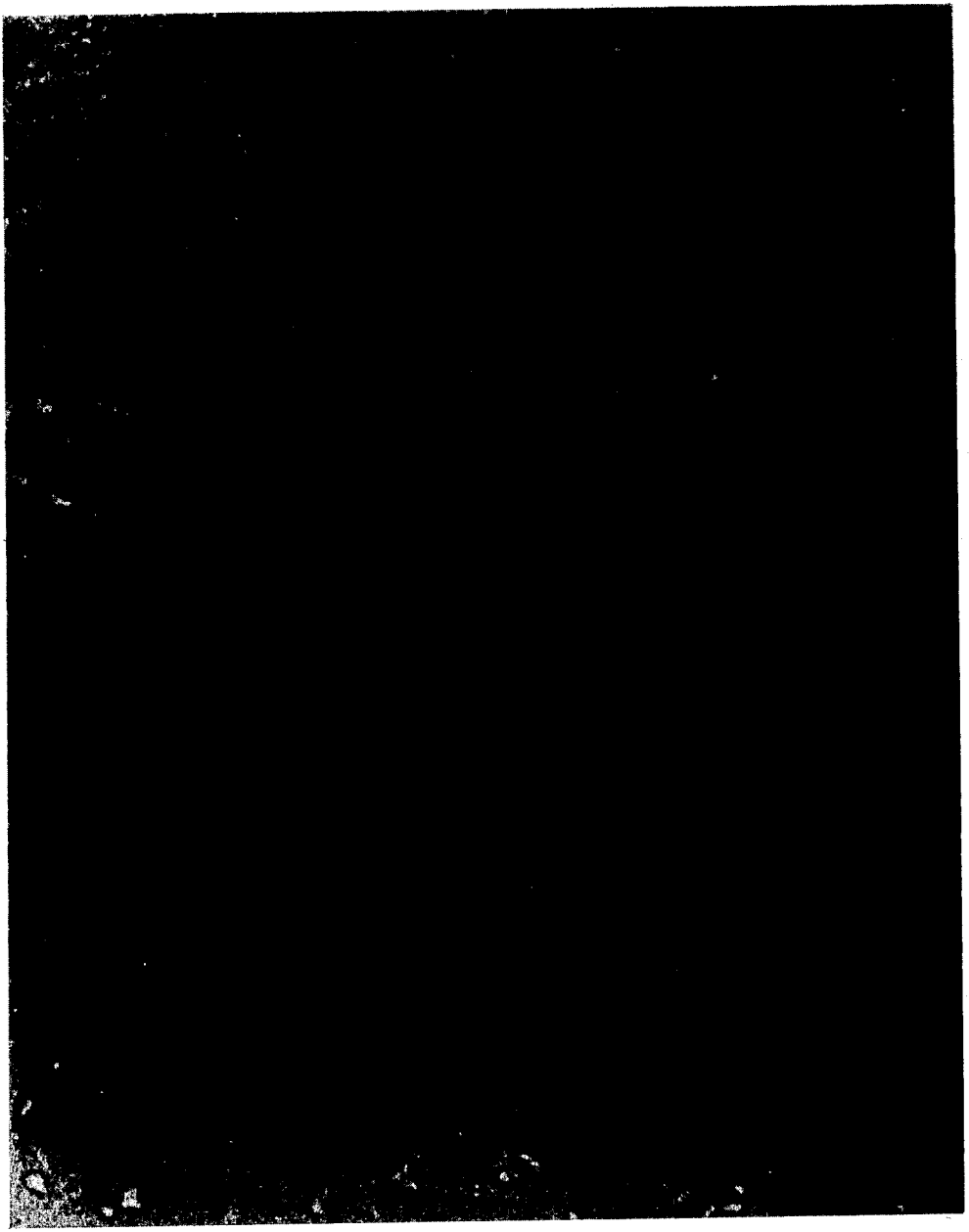
FIG. 1 shows a microscopic examination of filler frit, mix III.

This application is directed to subject matter discovered by the applicants and first disclosed at the Second Annual Meeting of the Society for Biomaterials in Philadelphia, Pennsylvania, Apr. 9–13, 1976, as part of a paper entitled "Microporous Glassy Fillers for Dental Composites (unpublished)." This application incorporates by reference the teachings of that paper.

Preparation of a novel filler according to this invention preferably involves gelling a refractory inorganic oxide gel, curing the sol, heating or pre-calcining the gel to remove nitrous oxides and calcining the gel to provide a microporous glassy filler and to effect grain densification of the filler. Preferred gels were prepared from sols containing $SiO_2$, $Al_2O_3$, $Zr(NO_3)_4$ and minor amounts of fluxing agents and peptizing agents.

These frits may be used with any commonly available resin system. A listing of the preferred resin system used when testing these novel frits is contained in Table I. The resin system however can contain about 50 to 80 wt. % BIS-GMA and 50 to 20 wt. % TEGDMA.

TABLE I

| | BIS-GMA and TEGDMA 70:30 Monomer Mixes | | | | |
|---|---|---|---|---|---|
| | Composition wt % | | | | |
| | Amine Fraction | | | Peroxide Fraction | |
| Preparation Designation | DHPT | DMPT | BHT | BP | BHT |
| 1 | 1.15 | — | — | 2.11 | 0.15 |
| 2 | 1.54 | — | — | 2.33 | 0.20 |
| 3 | 2.00 | — | — | 2.55 | 0.15 |
| 4 | 3.43 | — | — | 2.50 | 0.25 |
| 5 | 1.85 | — | — | — | — |
| 6 | 1.25 | — | — | 2.32 | 0.15 |
| 7 | 1.54 | 0.20 | 0.30 | — | — |
| 8 | — | — | — | 3.00 | 0.30 |

During preparation of the sols, silica was added in the form of acidic ethyl polysilicates, Silbond H-4 from Stauffer Chemical Co. Alumina was added as chloride stabilized acid sols, 5025 polymer from Hammil & Gillespie, Inc., and zirconium as zirconium carbonate paste from Magnesium Electron, Inc., dissolved in 70% nitric acid or, in a few instances, as zirconium acetate solutions from Magnesium Electron, Inc. In some preparations, tin was added as an x-ray opacifying agent, in addition to the zirconium. The tin was added to the gel mixture as an alcoholic solution (methanol) of hydrated tin chloride ($SnCl_4.5H_2O$). Hafnium or tantalum compounds may also be used as an x-ray opacifying agent.

Also Cab-O-Sil from Cabot Corp. was used to introduce part of the silica and effect rapid gelling.

Flux additions were made by dissolving one gram each of boric acid, sodium carbonate, lithium carbonate, and mono-ammonium phosphate in 100 cc of 3 wt % nitric acid. These prepared solutions were added in varying amounts to the gelling mixtures (Table II).

TABLE II

Composition of Gelling Mixtures

| Mix Desig- nation | Zirconium Carbonate Paste (40%ZrO$_2$) gm | Zirconium Acetate Soln (22%ZrO$_2$) ml | Tin Chloride Hydrate (SnCl$_4$·5H$_2$O) gm | Al$_2$O$_3$ Polymer (5025·22% Al$_2$O$_3$) ml | Silbond H-4 (18% SiO$_2$) ml | Cab-O-Sil (SiO$_2$) gm | Lithium Carbonate Soln ml | Sodium Carbonate Soln ml | Ammonium Phosphate Soln ml | Sodium Fluoride Soln ml | Boric Acid Soln ml | Nitric Acid (70%) ml | Methanol (Absol.) ml | Ethanol (Absol) ml | Glacial Acetic ml | H$_2$O (Additional) |
|---|---|---|---|---|---|---|---|---|---|---|---|---|---|---|---|---|
| I | | 125 | | 100 | 224 | | 1 | 1 | 1 | | 2 | 100 | | 660 | | 100 |
| II | | 150 | | 150 | 350 | | 10 | | 1 | | 5 | 200 | | 550 | | 80 |
| III | 24.4 | | | 150 | 122 | | 5 | | | | 10 | 61 | 750 | | | |
| IV | 48.0 | | | 100 | 250 | | 5 | | 10 | | 5 | 220 | 650 | | | 24 |
| V | 48.0 | | | 100 | 250 | | 5 | | | 5 | 5 | 320 | 550 | | | |
| VI | | 125 | | 100 | 250 | | 5 | | | | 5 | 300 | 650 | | | |
| VII | 47.2 | | | 104 | 250 | | 2 | 2 | 10 | | 2 | 468 | 550 | | | |
| VIII | 48.0 | | | 100 | 250 | | 3 | 3½ | 10 | | 5 | 470 | 550 | | | |
| IX | 48.0 | | | 100 | 250 | | 5 | | | | 10 | 470 | 550 | | | |
| X | 48.0 | | | 100 | 250 | | | | | | | 450 | 550 | | | |
| XI | 26.0 | | | 100 | 126 | | | | | 10 | | 470 | 550 | | | |
| XII | 26 | | | 50 | 100 | | 5 | 5 | | | 10 | 280 | 275 | | | |
| XIII | 26 | | | 50 | 100 | | 5 | 2 | | | 10 | 280 | 275 | | | |
| XIV | 26 | | | 50 | 130 | | 1 | 1 | | | 10 | 280 | 275 | | | |
| XV | | 100 | | 100 | 226 | | 1 | | | | 5 | 150 | 250 | | 50 | |
| XVI | | 100 | | 100 | 225 | | | 2.7 | | | 6 | 260 | 460 | | | |
| XVII | 16 | | | 50 | 130 | | | 2 | 1 | | 10 | 150 | 260 | | | |
| XVIII | 26 | | | 50 | 130 | | | 1 | 1 | | 10 | 280 | 250 | | | |
| XIX | 26 | | | 50 | 135 | | | 2 | 2 | 15 | 10 | 280 | 225 | | | |
| XX | 26 | | | 50 | 130 | | | 1 | 3 | | 280 | 200 | | | | |
| XXI | 26 | | | 50 | 100 | | | 2 | 1 | | 10 | 285 | 150 | | | |
| XXII | 26 | | | 50 | 102¼ | | 1 | 2 | 3¼ | | 15 | 280 | 200 | | | |
| XXIII | 26 | | | 50 | 100 | | 1 | 2 | 5 | | 10 | 280 | 250 | | | |
| XXIV | 26 | | | 50 | 130 | | 1 | 2 | 1 | | 10 | 280 | 200 | | | |
| XXV | 26 | | | 60 | 130 | | 2 | 2 | 2 | | 20 | 180 | 250 | | | |
| XXVI | 26 | | | 55 | 130 | | | 2½ | 1½ | | 10 | 180 | 200 | | | |
| XXVII | 26 | | | 50 | 130 | | | 2 | 1 | | 10 | 155 | 200 | | | |
| XXVIII | 26 | | | 75 | 135 | | 1½ | 2¼ | 1 | | 10 | 180 | 200 | | | |
| XXIX | 26 | | | 75 | 100 | | 10 | | 1½ | | 10 | 180 | 200 | | | |
| XXX | 26 | | | 60 | 130 | | 5 | | 5 | | 10 | 180 | 200 | | | |
| XXXI | 26 | | | 70 | 130 | | 20 | | 10 | | | 130 | 200 | | | |
| XXXII | 26 | | | 50 | 132 | | 3 | 2 | | | 2 | 180 | 200 | | | |
| XXXIII | 52 | | 35 | 50 | 100 | 39 | 10 | 5 | | | 12 | 200 | 200 | | | |
| | | | | | | | | | | | 20 | 224 | | | | |

Large amounts of alcohol (methanol and ethanol) and sometimes small amounts of glacial acetic acid were added to aid in peptization of the mixed sols.

Gelling of the mixed sol was consummated in large crystallization dishes (20.5 cm dia.) aided by heat application. The gelled mixture was then cured hard by heating for 24 hours on a surface temperature of approximately 250° C.

The gel can be cured at a temperature in the range of about 150°-300° C., and preferably about 200°-275° C. The time of cure is selected to provide hard product.

After this low temperature heat curing, the cured gel may be heated prior to calcination, or pre-calcined, to remove nitrous oxides. The mixtures were inserted on small cyrstallization dishes (10 cm diam.) into a muffle furnace and heated at 500° C. for 30 to 40 minutes. Subsequently, the samples were heated in large crystalization dishes in a forced air furnace from room temperature to 450° C. over a period of one hour. Pre-calcining heating, however, can be effected at temperatures of about 350°-650° C., or perferably at about 400°-550° C. The time of precalcination heating is about 15 minutes to about 3 hours. Preferred heating times are about 0.5 hours to 1.5 hours.

Various high temperature calcination procedures were used to effect densification of the pre-calcined frit. Approximate resulting compositions of these frits are shown in Table III.

ent firing times were used to attain various degrees of densification and the different refractive indices without excessive devitrification. Pulse heating was invariably used at the higher temperatures.

Repeated pulse heating was utilized to adjust the refractive index. After each pulse-heating, the sample was thoroughly churned up in the crucible after cooling down to room temperature. Preferably, the sample is permitted to cool to a temperature of about 25° to 100° C.

After each pulse-heat treatment, the refractive index of the frit is determined microscopically with oils. The median refractive index (white light) should preferably be less than 1.570 but more than 1.550. Ninety percent or more of the frit should have a refractive index ranging between 1.50 and 1.60. No more than 1 vol. % of microcrystalline material should be present. If the refractive index is not properly adjusted, heat treatment should be made more severe if the refractive index is too low and should be reduced in severity if the refractive index is too high.

Other firings were made by distributing approximately 25-50 gm amounts of pre-calcined powder over ten 0.5 mm thick, 5×5 cm alumina substrates which were passed at varying rates through an electric belt kiln. These loaded substrates were placed about one cm apart on the chain belt which passed through the electric kiln. Different peak temperatures and rates of pass

TABLE III

| Frit Designation | Composition of Calcined Frits, Approximate Mass Percent (Calculated) | | | | | | | | |
|---|---|---|---|---|---|---|---|---|---|
| | $ZrO_2$ | Sn | $Al_2O_3$ | $SiO_2$ | $B_2O_3$ | $P_2O_5$ | $Li_2O$ | $Na_2O$ | NaF |
| I | 35.16 | | 28.68 | 36.08 | 0.011 | 0.006 | 0.004 | 0.056 | |
| II | 29.77 | | 30.36 | 39.79 | 0.02 | 0.042 | 0.027 | | |
| III | 13.14 | | 59.55 | 27.20 | 0.08 | | 0.027 | | |
| IV | 21.29 | | 32.69 | 45.90 | 0.031 | 0.07 | 0.022 | | |
| V | 21.29 | | 32.69 | 45.91 | 0.031 | | 0.022 | | 0.055 |
| VI | 33.73 | | 27.52 | 38.64 | 0.021 | 0.058 | 0.019 | | |
| VII | 20.74 | | 33.68 | 45.48 | 0.011 | 0.068 | 0.009 | 0.012 | |
| VIII | 21.295 | | 32.71 | 45.93 | 0.031 | | 0.013 | 0.021 | |
| IX | 21.30 | | 32.70 | 45.92 | 0.060 | | 0.020 | | |
| X | 21.30 | | 32.70 | 45.99 | | | | 0.010 | |
| XI | 22.57 | | 31.98 | 45.29 | 0.12 | | 0.040 | | |
| XII | 22.25 | | 31.53 | 46.06 | 0.12 | | 0.040 | | |
| XIII | 22.24 | | 31.52 | 46.04 | 0.12 | 0.008 | 0.010 | 0.062 | |
| XIV | 22.25 | | 31.53 | 46.055 | 0.12 | 0.012 | 0.008 | 0.025 | |
| XV | 30.16 | | 30.75 | 39.04 | 0.03 | 0.007 | 0.005 | 0.007 | |
| XVI | 30.21 | | 30.80 | 38.93 | 0.038 | 0.015 | | 0.007 | |
| XVII | 22.24 | | 31.50 | 46.00 | 0.20 | 0.030 | | 0.030 | |
| XVIII | 22.25 | | 31.52 | 46.05 | 0.12 | 0.040 | | 0.02 | |
| XIX | 21.85 | | 30.97 | 46.98 | 0.18 | 0.010 | | 0.010 | |
| XX | 22.24 | | 31.52 | 46.04 | 0.12 | 0.050 | | 0.030 | |
| XXI | 22.22 | | 31.49 | 46.00 | 0.18 | 0.083 | | 0.027 | |
| XXII | 22.03 | | 31.22 | 46.47 | 0.12 | 0.13 | 0.008 | 0.022 | |
| XXIII | 22.22 | | 31.49 | 46.00 | 0.12 | 0.13 | 0.010 | 0.030 | |
| XXIV | 22.22 | | 31.49 | 45.99 | 0.240 | 0.026 | 0.008 | 0.026 | |
| XXV | 21.14 | | 35.50 | 43.20 | 0.105 | 0.020 | 0.015 | 0.020 | |
| XXVI | 21.54 | | 33.58 | 44.60 | 0.12 | 0.13 | | 0.030 | |
| XXVII | 22.22 | | 31.50 | 46.00 | 0.12 | 0.13 | | 0.030 | |
| XXVIII | 18.92 | | 40.23 | 40.69 | 0.102 | 0.02 | 0.013 | 0.025 | |
| XXIX | 19.22 | | 40.86 | 39.79 | | 0.056 | 0.074 | | |
| XXX | 20.92 | | 35.59 | 43.32 | | 0.125 | 0.045 | | |
| XXXI | 19.75 | | 39.19 | 40.88 | 0.020 | | 0.160 | | |
| XXXII | 28.18 | | 28.85 | 42.79 | 0.130 | | 0.025 | 0.025 | |
| XXXIII | 19.32 | 10.60 | 13.69 | 56.21 | 0.10 | | 0.05 | 0.030 | |

Most firings of frits were made in a muffle furnace. Before firing, all pre-calcined frits were ground through 100 mesh. Approximately 50 gram charges of pre-calcined powder were put into porcelain crucibles. Differthrough were investigated. Temperature profiles rose linearly to a peak and quickly dropped. Peak temperatures were varied according to the procedures shown in Table IV.

TABLE IV

Frit Calcination Conditions

| Frit Designation | Furnace | \multicolumn{8}{c}{Heat Treatments, °C.} |
|---|---|---|---|---|---|---|---|---|---|
| | | 1st | 2nd | 3rd | 4th | 5th | 6th | 7th | 8th |
| I | Muffle[a] | 760–860, 45° | | | | | | | |
| II-1 | " | 500, 6 hr. | 920, 1° | 920, 3° | 610, 45° | | | | |
| II-2 | " | 500, 4 hr. 40° | 910, 12° | | | | | | |
| II-3 | " | 500, 4 hr. 40° | 920, 12° | 930 3° | | | | | |
| III | " | 500, 2 hr. | 940, 35° | | | | | | |
| IV | " | 500, 17 hr. | 600, 7 hr. | 650, 12 hr. | | | | | |
| V | " | 860–995, 28° | | | | | | | |
| VI-1 | " | 650, 24 hr. | | | | | | | |
| VI-2 | " | 650, 24 hr. | 950, 1° | | | | | | |
| VII-1 | Forced air | 450, 1 hr. | | | | | | | |
| VII-2 | Muffle | 450, 3 hr. | 200–210, 1 hr. | | | | | | |
| VIII-1 | " | 545, 22 hr. | | | | | | | |
| VIII-2 | " | 545, 22 hr. | 550–550, 1 hr. | | | | | | |
| IX | " | 975, 2° | | | | | | | |
| X-1 | " | 550, 1 hr. | 875, 4° | | | | | | |
| X-2 | " | 550, 1 hr. | 875, 4° | 500–670, 11° held | 670, 2 hr. | | | | |
| X-3 | " | 550, 1 hr. | 875, 4° | | | 930, 1° | 550, 17 hr. | | |
| XI | " | 400–555, 45° | 500–670, 25° | | | | | | |
| XII | " | 530–660, 15° | 580–770, 30° | | | | | | |
| XIII-1 | " | 770–820, 42° | 850–960, 15° | | | | | | |
| XIII-2 | " | 910–970, 8¼° | | | | | | | |
| XIV-1 | " | 770–920, 24° | 850–900, 10½° | | | | | | |
| XIV-2 | " | 810–880, 5¾° | 820–895, 5° | 910, 8° | | | | | |
| XIV-3 | " | 860–960, 10° | | | | | | | |
| XIV-4 | " | 895–940, 3° | 920–965, 3¾° | | | | | | |
| XV-1 | " | 630–805, 27° | | | | | | | |
| XV-2 | " | 630–805, 27° | | | | | | | |
| XVI-1 | " | 500–630, 25° | | | | | | | |
| XVI-2 | " | 580–775, 26° | | | | | | | |
| XVII-1 | " | 770–900, 19° | 820–890, 19° | 820–915, 19° | 840–950, 16° | | | | |
| XVII-2 | belt[b] | 975 4° min | | | | | | | |
| XVIII | Muffle | 850–960, 16° | 890–980, 15½° | | | | | | |
| XIX | " | 970–1030, 4° | 1000–1040, 3° | | | | | | |
| XX | Belt | 950 12° min. | 920 85° min. | | | | | | |
| XXI | Muffle | 900, 12° | | | | | | | |
| XXII | " | 430–720, 40° | 730–810, 11° | 805–890, 11° | 800–925, 20½° | 900–930, 3° | 892–970, 9° | 910–970, 4° | |
| XXIII | Belt | 955 12° min. | | | | | | | |
| XXIV | " | 975, 4° min. | | | | | | | |
| XXV-1 | " | 920 | | | | | | | |

TABLE IV-continued

Frit Calcination Conditions

| Frit Desig-nation | Furnace | 1st | 2nd | 3rd | 4th | 5th | 6th | 7th | 8th |
|---|---|---|---|---|---|---|---|---|---|
| XXV-2 | " | 920, 1° min. | | | | | | | |
| XXV-3 | " | 920, 0.5° min. | | | | | | | |
| XXV-4 | " | 920, 0.8° min. | | | | | | | |
| XXVI | Muffle | 970–1010, 5° | 980–1030, 4¼° | 990–1030, 1¼° | | | | | |
| XXVII-1 | Belt | 950, 5° min. | | | | | | | |
| XXVII-2 | " | 950, 2° min. | | | | | | | |
| XXVII-3 | " | 950, 45° min. | | | | | | | |
| XXVIII | Muffle | 910–963, 8° | | | | | | | |
| XXIX | " | 880–980, 14° | | | | | | | |
| XXX-1 | " | 850–970, 8¼° | 890–980, 5° | 920–990, 5° | 910–975, 5° | 940–980, 3¼° | 910–1000, 5° | 980–1010, 5° | |
| XXX-2 | " | 910–1010, 17½° | | | | | | | |
| XXXI | " | 1010–1060, 3° | | | | | | | |
| XXXII | " | 800–870, 4° | 840–870, 4° | | | | | | |
| XXXIII | " | 980–1010, 2¼° | 1020–1050, 1¾° | 1020–1040, 1° | 1020–1040, ½° | 1020–1040, ½° | 1020–1040, ½° | 1020–1040, 1 1/6° | 1020–1040, 2/3° |

<sup>a</sup>Electric muffle furnace, Lindberg Div. Sole Basic Industries, 2450 W. Hubbard St., Chicago, Ill. 60612. Type 86, Serial No. 19497, 230 volts, 18 amps., 50–60 cycles, max. temp. 1000° C.
<sup>b</sup>Electric belt kiln, Polytherm Inc., Div. IMS Corp. 205 Sylvan Rd. Woburn, Mass. 01801. Belt furnace #2, Conveyor Model CAR 1003, Serial #13099, Power, 208 volts three phase: Controls, 110 volts, 40 amperes.

The rapid-firing electric belt kilns are preferable to muffle furnaces in pulse heating. The kilns should be capable to complete pass through times as low as 10–30 minutes, preferably 15–20 minutes. For every kiln, temperature profile and rate of pass through has to be adjusted to give the desired frit refractive index and minimum crystallinity. In general, the temperature profile should be run up sharply with a linear slope of at least 45° C./minute, but no greater than 75° C./minute.

Peak temperatures should preferably be no higher than about 1000° C., preferably no higher than 975° C., and no lower than 800° C., preferably no lower than 870° C. Rate of pass through and number of firings should be adjusted to give the proper frit properties. Pre-calcined or defumed frits should be passed as about 25–50 gram charges spread over ten, dense alumina substrates (0.05×5×5 cm).

Alternatively, calcination could involve heating the pre-calcined frit over a prolonged period of time, preferably two hours or more, at temperatures of between about 500° and 800° C. The calcination procedure, whether by prolonged heating or by high temperature pulse heating, can be preferably adjusted to produce a filler having a density of about 2.57 to about 3.15 grams per milliliter and to adjust the refractive index of the microporous glassy filler to about 1.51 to about 1.64.

After completion of the firings, the refractive indices of crushed frit grain were determined with an optical microscope by the immersion method. Both the median and the range in the refractive index were determined. Also estimated were the volume percent crystals and opalescent vitreous regions. (Table V).

TABLE V

| | Frit Filler Grain Properties | | | | | | | | |
|---|---|---|---|---|---|---|---|---|---|
| Frit-Desig-nation | Refractive Indices | | Vol. % crys-tals | Vol. % Opal-escent Regions | Sieve Size | | Density gm/cc | | |
| | Range | Median | | | Vol. % +200 | Vol. % −400 | Mean | h | Range |
| I | 1.535–1.620 | 1.578 | 2 | — | — | 91.0 | 2.94 | 1 | — |
| II-1 | 1.530–1.500 | 1.555 | 1 | — | — | 93.5 | 2.61 | 2 | ±0.02 |
| II-2 | 1.536–1.572 | 1.554 | 2 | — | — | 100.0 | 2.76 | 2 | ±0.01 |
| II-3 | 1.532–1.566 | 1.549 | 1 | — | — | 92.5 | 2.915 | 2 | ±0.005 |
| III | 1.548–1.596 | 1.572 | 10 | — | 48.9 | 26.4 | 2.775 | 2 | ±0.005 |
| IV | 1.532–1.594 | 1.563 | 1 | — | — | 94.1 | 2.765 | 2 | ±0.015 |
| V | 1.572–1.590 | 1.581 | 1–5 | — | — | 41.5 | 2.895 | 2 | ±0.025 |
| VI-1 | 1.534–1.560 | 1.547 | 1 | — | 13.5 | 52.4 | 2.56 | 1 | — |
| VI-2 | 1.510–1.582 | 1.546 | 1 | — | 8.8 | 52.7 | 2.85 | 1 | — |
| VII-1 | 1.494–1.586 | 1.540 | 2 | 10 | — | 73.4 | 2.48 | 1 | — |
| VII-2 | 1.520–1.560 | 1.540 | 1–5 | — | — | 75.3 | 2.48 | 2 | ±0.01 |
| VIII-1 | 1.528–1.612 | 1.570 | 1 | 5 | — | 93.9 | 2.72 | 1 | — |
| VIII-2 | 1.512–1.552 | 1.532 | 2 | 10 | — | 91.3 | 2.63 | 1 | — |

TABLE V-continued

| Frit-Designation | Refractive Indices Range | Refractive Indices Median | Vol. % crystals | Vol. % Opalescent Regions | Sieve Size Vol. % +200 | Sieve Size Vol. % −400 | Density gm/cc Mean | h | Range |
|---|---|---|---|---|---|---|---|---|---|
| IX | 1.526–1.570 | 1.548 | 2 | 50 | 83.0 | 10.6 | 2.60 | 2 | ±0.03 |
| X-1 | 1.530–1.575 | 1.553 | 2 | — | — | 80.2 | 2.54 | 2 | ±0.02 |
| X-2 | 1.524–1.560 | 1.542 | 5 | — | — | 86.3 | 2.62 | 1 | — |
| X-3 | 1.536–1.580 | 1.558 | 10 | — | — | 88.3 | 2.59 | 1 | — |
| XI | 1.480–1.580 | 1.530 | 2 | — | — | 67.4 | 2.52 | 1 | — |
| XII | 1.528–1.568 | 1.648 | 1 | 5 | — | 47.4 | 2.54 | 1 | — |
| XIII-1 | 1.534–1.676 | 1.605 | 10 | 50 | | 90.9 | 2.71 | 1 | — |
| XIII-2 | 1.510–1.618 | 1.564 | 1 | 10 | — | 45.3 | 2.79 | 1 | — |
| XIV-1 | 1.516–1.648 | 1.582 | 1 | — | — | 78.4 | 2.985 | 1 | — |
| XIV-2 | 1.524–1.624 | 1.574 | 1 | — | — | 94.8 | 2.70 | 1 | — |
| XIV-3 | 1.620–1.656 | 1.639 | 1 | — | — | 73.3 | 3.15 | 1 | — |
| XIV-4 | n.d.[b] | n.d. | n.d. | n.d. | — | n.d. | 2.79 | 1 | — |
| XV-1 | 1.536–1.580 | 1.558 | 25 | — | — | 82.8 | 2.63 | 1 | — |
| XV-2 | 1.524–1.594 | 1.559 | 1–3 | — | — | 72.9 | 2.60 | 1 | — |
| XVI-1 | 1.538–1.580 | 1.559 | 2–5 | — | 16.5 | 47.9 | 2.645 | 2 | ±0.005 |
| XVI-2 | 1.540–1.594 | 1.567 | 10 | — | 16.9 | 45.8 | 2.67 | 1 | — |
| XVII-1 | 1.524–1.576 | 1.550 | 1 | — | — | 92.0 | 2.80 | 1 | — |
| XVII-2 | 1.580–1.638 | 1.609 | 3 | — | — | 75.9 | 2.99 | 1 | — |
| XVIII | 1.530–1.639 | 1.580 | 1 | — | — | 92.6 | 2.82 | 1 | — |
| XIX | 1.498–1.576 | 1.537 | 3 | — | 21.6 | 40.4 | 2.67 | 1 | — |
| XX-1-2 | 1.524–1.604 | 1.564 | 1 | 10 | — | 94.2 | 2.76 | 1 | — |
| XXI | 1.458–1.558 | 1.508 | 1 | 20 | — | 17.3 | 2.53 | 1 | — |
| XXII | 1.482–1.602 | 1.542 | 1 | — | — | 58.9 | 2.62 | 1 | — |
| XXIII-1 | 1.594–1.650 | 1.582 | 1 | 1 | 61.3 | 25.4 | 2.82 | 1 | |
| XXIV | 1.590–1.640 | 1.615 | 2 | — | 27.0 | 46.5 | 3.12 | 1 | — |
| XXV-1 | 1.524–1.594 | 1.559 | 2 | — | — | 10.9 | 2.78 | 1 | — |
| XXV-2 | 1.548–1.598 | 1.573 | 25 | — | 21.4 | 49.5 | 2.91 | 1 | — |
| XXV-3 | 1.530–1.590 | 1.560 | 1 | 20–40 | 60.3 | 37.1 | 2.79 | 1 | — |
| XXV-4 | 1.550–1.610 | 1.580 | 5 | — | — | 96.7 | 2.81 | 1 | — |
| XXVI | 1.520–1.594 | 1.557 | 5–10 | — | — | 82.6 | 2.56 | 1 | — |
| XXVII-1 | 1.528–1.616 | 1.572 | 1 | — | 34.4 | 31.0 | 2.77 | 1 | — |
| XXVII-2 | 1.570–1.650 | 1.610 | 1 | 5–10 | 28.4 | 36.7 | 2.80 | 1 | — |
| XXVII-3 | 1.542–1.614 | 1.578 | 2 | — | — | 53.4 | 2.92 | 1 | — |
| XXVIII | 1.536–1.612 | 1.574 | 1 | — | — | 92.7 | 2.61 | 1 | — |
| XXIX | 1.604–1.660 | 1.632 | 5 | — | 12.4 | 47.5 | 3.02 | 1 | — |
| XXX-1 | 1.540–1.578 | 1.559 | 5 | — | 8.6 | 47.9 | 2.70 | 1 | — |
| XXX-2 | 1.550–1.676 | 1.613 | 1–2 | — | 13.2 | 51.6 | 2.89 | 1 | — |
| XXXI | 1.520–1.594 | 1.557 | 3 | — | 10.0 | 54.5 | 2.37 | 1 | — |
| XXXII | 1.498–1.598 | 1.548 | — | 40 | — | 93.6 | 2.75 | 1 | |
| XXXIII | 1.576–1.606 | 1.566 | 1 | — | 2.5 | 68.2 | 2.80 | 1 | |

[a]U.S. Standard Sieves.
[b]Not determined.

Fully fired frit grain was milled in porcelain pebble mills loaded to varying degrees with Belgian flint pebbles. Particle size was characterized by means of 4 inch diameter 200- and 400-mesh screens.

One gram representative splits were screened dry through 200-mesh by hand rotapping for 10 minutes. The plus-200-mesh material was weighed. Separate one-gram samples were wet screened in absolute methanol through the 400-mesh screen and collected in small crystallization dishes and the collected slurry was thoroughly dried on a hot plate. Then weight pickup on the crystallization dishes was determined and weight percentages of plus-200 and minus-400 material were calculated (Table V).

Milling and particle size classification procedures are adjusted so that no plus-200-mesh frit particles are present, and so that 85–90 vol % of the frit is minus-400-mesh. After stage grinding in a large mullite mortar through 100-mesh, 50-gram frit charges are placed in a 1-quart porcelain mill half loaded by bulk volume with fully cleaned Belgian flint. In the milling extreme fines are to be minimized without sacrificing strength so that the maximum amount of filler can be put into a two-component paste system which autocatalyzes upon mixing.

Densities of the frit powders as milled were determined in distilled water using standard pycnometer techniques. Pycnometers with 25 ml capacity were used with the amounts of powder for each determination varying from 0.5 to 3 grams (Table V). Using the described techniques, particle sieve size and powder densities were also determined (Table VI) for current available commercial fillers.

TABLE VI

| | | Commercial Filler Grain Properties | | | | | | |
|---|---|---|---|---|---|---|---|---|
| | Grain Description | | Treatment | | Sieve Size | | Density gm/cc | | |
| Grain Designation | Source Designation | | Leaching | Roasting | Vol.% +200 | Vol.% −400 | Mean | n | Range |
| A | Corning Glass[b] 1720, −325 mesh | | — | — | — | 89.0 | 2.56 | 1 | — |
| B | Fused Quartz[c] Chips | | — | — | — | 74.9 | 2.22 | 1 | — |

TABLE VI-continued

Commercial Filler Grain Properties

| Grain Designation | Grain Source Designation | Treatment Leaching | Treatment Roasting | Sieve Size Vol.% +200 | Sieve Size Vol.% −400 | Density gm/cc Mean | n | Range |
|---|---|---|---|---|---|---|---|---|
| C | Pennsylvania[d] Glass Sand Morgan 200 | — | 650° C., 1 hr. | — | 75.4 | 2.66 | 1 | — |
| D | Ottawa Silica[e] 400 mesh (milled) | 70% HNO$_3$ | 800° C., 1 hr. | — | 90.0 | 2.64 | 2 | ±0.04 |
| E | Min-U-Sil[d] | 70% HNO$_3$ | 870° C., 1 hr. | — | 100.0 | 2.61 | 1 | — |
| F | Ottawa Silica[e] 400 mesh | — | 760° C., | — | 71.3 | 2.64 | 1 | — |
| G | Ottawa Silica[e] 400 mesh | 70% HNO$_3$ | 800° C., 1 hr. | — | 71.5 | 2.67 | 1 | — |
| H | Juniata[d] Opal | 70% HNO$_3$ | 800° C., 1 hr. | — | 72.2 | 2.64 | 1 | — |
| I | Pennsylvania[d] Glass Sand, Low Iron | 70% HNO$_3$ | 800° C., 1 hr. | 1.1 | 64.0 | 2.61 | 1 | — |
| J | Pennsylvania[d] Glass Sand, Juniata | 70% HNO$_3$ | 800° C., 1 hr. | — | 72.3 | 2.61 | 1 | — |
| K | Ottawa Silica[e] #200 Mystic Connecticut Willey Milled[c] | 70% HNO$_3$ | 800° C., 1 hr. | 14.8 | 44.1 | 2.63 | 1 | — |
| L | Fused Quartz Wool | — | — | — | 100.0 | 2.22 | — | — |
| M | Cab-O-Sil[f] Grade M-5 | — | — | — | 100.0 | 2.22 | — | — |

[a]U.S. Standard Sieves
[b]Corning Glass Corp., Corning, N.Y.
[c]Thermal American Fused Quartz Co., Route 202 and Change Bridge Rd Montville, N.J.
[d]Pennsylvania Glass Sand Corp., 200 Three Penn Center, Pittsburgh, Pa.
[e]American Graded Co., 352 E. Howard Des Plaines, Illinois
[f]Cabot Corp., 125 High St., Boston, Mass.

Frits were treated with Silane A174 (Union Carbide Co., Tarrytown, N.Y.). About ½ percent by weight of the powder was added as silane dissolved in acetone. The coated powders were let to dry at room temperature under a hood. These were then subjected to an aspirator vacuum in vacuum oven set at 70° C. for 12 hours. Powders were thoroughly washed in acetone and vacuum filtered through a Buchner funnel. After filtering, the powders were retreated at 70° C. as before. If the pressed coated powders did allow a droplet of distilled water to penetrate after five minutes standing, silane treatment was again applied.

EXAMLE I

A procedure for the preparation of a typical embodiment of the frit utilized in the invention is set forth below.

Twenty-six grams of zirconium carbonate paste (40% ZrO$_2$) are dissolved in 280 ml of 70% HNO$_3$ to which is added the following 1 wt% aqueous solutions: Li$_2$CO$_3$, 1 ml; Na$_2$CO$_3$, 2 ml; NH$_4$H$_2$PO$_4$, 1 ml, and H$_3$BO$_3$, 10 ml. Then 50 ml of chloride stabilized alumina sol, containing 22 wt% Al$_2$O$_3$ (5025 polymer, Hammill and Gillespie, New York, N.Y.) and then 250 ml of absolute methanol are added to the above solution. To this prepared mixture is added 130 ml of 18 wt% SiO$_2$ alcoholic silica (Silbond H-4, Stauffer Chemical Co., Weston, Mich.).

Gelling is consummated in large crystallization dishes (20.5 cm. dia., 10 cm. ht.) aided by heat application from a hot plate. The gelled mixture is then cured hard by heating 24 hours on a hot plate with a surface temperature of approximately 250° C.

The hardened gel is then mounted in small pyrex crystallization dishes and heated at 500° C. for 30–40 minutes to eliminate nitrous oxides. This powder is then placed in a forced-air kiln and heated about 1 hour to a peak temperature of 450° C.

Pre-calcined, 500° C. heated frit is placed in 50 gram amounts into porcelain crucibles having the following dimensions: aperture, 6.35 cm; base, 2.54 cm; and height, 5.70 cm. Each crucible is pulse-heated in a Lindberg electric muffle furnace (230 volt, 18 amp., 50–60 cycle, Sola Basic Industries, Chicago, Ill.). After each pulse-heating, the sample is thoroughly churned up in the crucible with a procelain spatula ater cooling down to within 50° C. of room temperature. The pulse-heating cycle with the furnace couple placed over the sample is 895°–940° C., 3 min.; cool; and 920°–965° C., 3¼ min.

The repeated pulse-heating is continued until the filler material attains a desirable refractive index. Following the pulse-heating the filler material was milled and treated with silane as described heretofore.

Blends of the various commercial grain filler with one another and with experimental frit product were made (Tables VII and VIII) for testing of resin composites. These blends were made by blending overnight (12 hrs.). Silane treatment of the commercial grain and blends was made by the procedures used for the experimental frits.

TABLE VII

Commercial Filler Blend Compositions

| Blend Designation | Composition Components General Description | Grain Designation | Wt.% Components | Sieve Size[a] (Computed) Vol.% −400 |
|---|---|---|---|---|
| a - B, L | Fused Quartz Chips | B | 80.0 | 79.9 |
|  | Willey Milled Fused Quartz Wool | L | 20.0 |  |
| b - B, L | Fused Quartz Chips | B | 66.7 |  |
|  | Willey Milled Fused Quartz Wool | L | 33.3 | 83.3 |
| c - B, L | Fused Quartz Chips | B | 50.0 |  |
|  | Willey Milled Fused Quartz Wool | L | 50.0 | 87.45 |
| d - B, L | Fused Quartz Chips | B | 90.0 |  |
|  | Willey Milled Fused Quartz Wool | L | 10.0 | 77.4 |
| e - L, B | Willey Milled Fused Quartz Wool | L | 75.0 |  |
|  |  |  |  | 93.7 |
|  | Fused Quartz Chips | B | 25.0 |  |
| f - F, L | Ottawa Silica 400 Mesh | F | 73.4 |  |
|  |  |  |  | 92.4 |
|  | Willey Milled Fused Quartz Wool | L | 26.6 |  |
| g - F, L | Ottawa Silica 400 Mesh | F | 50.0 |  |
|  |  |  |  | 86.9 |
|  | Willey Milled Fused Quartz Wool | L | 50.0 |  |
| h - F, L | Ottawa Silica 400 Mesh | F | 90.1 |  |
|  |  |  |  | 92.4 |
|  | Willey Milled Fused Quartz Wool | L | 9.9 |  |
| i - L, F | Willey Milled Fused Quartz Wool | L | 75.0 |  |
|  |  |  |  | 97.7 |
|  | Ottawa Silica 400 Mesh | F | 25.0 |  |
| j - C, L | Pennsylvania Glass Sand, Morgan 200 | C | 50.0 |  |
|  |  |  |  | 88.7 |
|  | Willey Milled Fused Quartz Wool | L | 50.0 |  |
| k - C, L | Pennsylvania Glass Sand, Morgan 200 | C | 95.0 |  |
|  |  |  |  | 76.8 |
|  | Willey Milled Fused Quartz Wool | L | 5.0 |  |
| l - C, F | Pennsylvania Glass Sand, Morgan 200 | C | 50.0 |  |
|  |  |  |  | 73.35 |
|  | Ottawa Silica 400 Mesh | F | 50.0 |  |
| m - C, F | Pennsylvania Glass Sand, Morgan 200 | C | 75.0 |  |
|  |  |  |  | 74.4 |
|  | Ottawa Silica 400 Mesh | F | 25.0 |  |
| n - C, F, L, E | Pennsylvania Glass Sand, Morgan 200 | C | 25.0 |  |
|  | Ottawa Silica 400 Mesh | F | 25.0 |  |
|  |  |  |  | 87.3 |
|  | Willey Milled Fused Quartz Wool | L | 25.0 |  |
|  | Min-U-Sil | E | 25.0 |  |
| o - E, C, F | Min-U-Sil | E | 50.0 |  |
|  | Pennsylvania Glass Sand, Morgan 200 | C | 25.0 | 86.8 |
|  | Ottawa Silica 400 Mesh | F | 25.0 |  |
| p - C, E, M | Pennsylvania Glass Sand, Morgan 200 | C | 50.0 |  |
|  |  |  |  | 87.9 |
|  | Min-U-Sil | E | 47.5 |  |
|  | Cab-O-Sil Grade M-5 | M | 2.5 |  |
| q - G, L | Ottawa Silica 398 Mesh | G | 75.0 |  |
|  | Willey Milled Fused Quartz Wool | L | 25.0 | 79.6 |
| r - K, L | Ottawa Silica, Mystic Conn. #200 | K | 75.0 |  |
|  |  |  |  | 59.8 |
|  | Willey Milled Fused Quartz Wool | L | 25.0 |  |

[a]No +200 Mesh material

TABLE VIII

Commercial and Frit Filler Blend Compositions

| Blend Designation | General Description | Grain Designation | Wt % | Sieve Size Vol.% +200 | (Computed) Vol.% −400 |
|---|---|---|---|---|---|
| 1-[I],E,L | Experimental frit | I | 50.0 | | 96.0 |
| | Min-U-Sil | E | 25.0 | — | |
| | Willey Milled Fused Quartz Wool | L | 25.0 | | |
| 2-[I],F,E,L | Experimental frit | I | 50.0 | | |
| | Ottawa Silica 400 Mesh | F | 25.0 | — | 93.2 |
| | Min-U-Sil | E | 12.5 | | |
| | Willey Milled Fused Quartz Wool | L | 12.5 | | |
| 3-[I],E,L | Experimental frit | I | 83.0 | | |
| | Min-U-Sil | E | 8.5 | — | 91.7 |
| | Willey Milled Fused Quartz Wool | L | 8.5 | | |
| 4-E,[I] | Min-U-Sil | E | 60.0 | | 96.7 |
| | Experimental frit | I | 40.0 | — | |
| 5-C,[I],M | Pennsylvania Glass Sand Morgan 200 | C | 69.0 | | 80.0 |
| | Experimental frit | I | 30.5 | — | |
| | Cab-O-Sil Grade M-5 | M | 0.5 | | |
| 6-IV,C | Experimental frit | IV | 50.0 | | 84.5 |
| | Pennsylvania Glass Sand Morgan 200 | C | 50.0 | — | |
| 7-IV,C | Experimental frit | IV | 75.0 | | 89.4 |
| | Pennsylvania Glass Sand Morgan 200 | C | 25.0 | — | |
| 8-C,IV | Pennsylvania Glass Sand Morgan 200 | C | 75.0 | — | 80.1 |
| | Experimental frit | IV | 25.0 | | |
| 9-IV,A | Experimental frit | IV | 50.00 | — | 91.6 |
| | Corning Glass 1720 (-325) | A | 50.0 | | |
| 10-[II-3],A | Experimental frit | II-3 | 75.0 | | 91.6 |
| | Corning Glass 1720 (-325) | A | 25.0 | — | |
| 11-A,[II-3] | Corning Glass 1720 (-325) | A | 57.5 | | 90.4 |
| | Experimental frit | II-3 | 42.5 | — | |
| 12-D,[II-1],L | Ottawa Silica 400 Mesh | D | 50.0 | | |
| | Experimental frit | II-1 | 32.0 | — | 71.0 |
| | Willey Milled Fused Quartz Wool | L | 18.0 | | |
| 13-[XVII-1],A,L | Experimental frit | XVII-1 | 67.8 | | |
| | Corning Glass 1720 (-325) | A | 26.1 | — | 91.8 |
| | Willey Milled Fused Quartz Wool | L | 6.1 | | |
| 14-[XIX],A,L | Experimental frit | XIX | 68.2 | | |
| | Corning Glass 1720 (-325) | A | 26.2 | 14.4 | 57.3 |
| | Willey Milled Fused Quartz Wool | L | 5.6 | | |

Preparation of the various quartz and natural silica commercial grains involved a prolonged heating at 500° C. for 16 hrs. After this heating the commercial grains were roasted at temperatures between about 650° and 870° C. for one hour in a muffle furnace. Before the silicas were roasted, they were leached in 70% nitric acid to make removal of organic material easier. Nitric acid was removed by washing and filtration. Density and sieve size determinations were made utilizing the procedures used for experimental frit (Table VI).

Preparation of a complete dental composite according to this invention involves the preparation of a resin, the novel filler and the mixture of a paste using the resin and filler.

The resin system used in preparing a complete dental composite for testing of the invention was 2,2-bis [4-(3 methacryloxy-2-hydroxy propoxy)-phenyl]- propane, or BIS-GMA, and tri-ethylene glycol - dimethacrylate, or TEGMA, in the ratio of 70% to 30% respectively, and a catalyst.

The catalyst used was either benzoyl peroxide, (BP) or dihydroxyethyl p-toluidine, (DHPT). Catalyst concentrations were adjusted in the resin system to give a proper setting time for the various filler systems used. Butylated hydroxy toluene, 2,6-di-t-butyl-p-methyl phenol, or BHT, was added in small amounts for stabilization of the monomer mix (Table 1).

The DHPT, dihydroxyethyl-p-toluidene, and the BP, benzoyl peroxide, are dissolved in suitable amounts of TEGDMA, tri-ethylene glycol-dimethacrylate, before adding the highly viscous BIS-GMA. These TEGDMA solutions should, when mixed with BISGMA, have 1.25 wt% DHPT in one liquid catalyst system and 2.32 wt% BP along with 0.15 wt% BHT in the other. Appropriate U.V. absorbers should then be added as necessary. The TEGDMA and the BISGMA should be mixed in the weight ratio, TEGDMA:- BISGMA, 30:70 preferably.

A liquid amine, N,N-dimethyl-p-toluidine or DMPT, was added in small amounts to one resin preparation (Table 1). However, this amine when used as the sole amine catalyst did not appear to yield the snap sets of the solid amine and appeared to be more susceptible to oxygen inhibition.

The BP and the DHPT resin pastes were mixed with various blends of filler. To a given amount of weighted filler a sufficient monomer liquid was added to attain a paste of satisfactory consistency. DHPT and BP concentration in the monomer liquid had to be adjusted to obtain reasonable setting times (Tables I and IX).

Table IX

Composition of Pastes

| Mix No. | Filler | Amine (monomer Liquid) | Benzoyl Peroxide (monomer Liquid) | Filler Content Amine Paste wt % | Filler Content Peroxide Paste wt % |
|---|---|---|---|---|---|
| 1 | C | 1 | 2 | 80.4 | 72.3 |
| 2 | F | 1 | 4 | 79.7 | 74.2 |
| 3 | B | 1 | 1 | 73.1 | 76.4 |
| 4 | E | 1 | 1 | 65.0 | 70.0 |
| 5 | I | 1 | 1 | 73.0 | 73.0* |
| 6 | V | 1 | 1 | 74.0 | 73.2 |
| 7 | IV | 1 | 1 | 67.0 | 64.7 |
| 8 | A | 1 | 1 | 70.2 | 71.4 |
| 9 | III | 1 | 1 | 74.2 | 76.5 |
| 10 | II-2 | 1 | 1 | 71.7 | 57.1 |
| 11 | II-3 | 1 | 1 | 72.0 | 74.6 |
| 12 | D | 1 | 1 | 75.4 | 75.0 |
| 13 | C | 1 | 1 | 75.4 | 76.6 |
| 14 | II-1 | 1 | 1 | 75.3 | 71.2 |
| 15 | K | 1 | 3 | 77.2 | 77.3 |
| 16 | I | 1 | 1 | 78.4 | 75.0 |
| 17 | J | 1 | 2 | 82.0 | 71.2 |
| 18 | K | 1 | 1 | 73.6 | 70.8 |
| 19 | a | 1 | 1 | 72.4 | 76.9 |
| 20 | b | 1 | 1 | 74.3 | 72.9 |
| 21 | c | 1 | 1 | 71.0 | 70.6 |
| 22 | d | 1 | 1 | 76.6 | 76.6* |
| 23 | e | 1 | 1 | 76.1 | 74.1 |
| 24 | f | 1 | 4 | 73.7 | 73.2 |
| 25 | g | 1 | 1 | 66.0 | 65.9 |
| 26 | h | 1 | 2 | 75.2 | 69.7 |
| 27 | i | 1 | 1 | 71.2 | 70.6 |
| 28 | j | 1 | 1 | 71.4 | 68.7 |
| 29 | k | 1 | 3 | 76.7 | 76.0 |
| 30 | l | 1 | 2 | 79.1 | 71.7 |
| 31 | m | 1 | 2 | 77.3 | 68.1 |
| 32 | n | 1 | 1 | 66.3 | 63.3 |
| 33 | o | 1 | 1 | 73.4 | 69.4 |
| 34 | p | 1 | 3 | 65.5 | 71.3 |
| 35 | 1 | 1 | 1 | 71.1 | 70.4 |
| 36 | 2 | 1 | 1 | 75.4 | 75.3 |
| 37 | 3 | 1 | 1 | 78.0 | 71.2 |
| 38 | 4 | 1 | 3 | 77.8 | 73.1 |
| 39 | 5 | 1 | 1 | 72.3 | 74.2 |
| 40 | 6 | 1 | 1 | 69.0 | 79.8 |
| 41 | 7 | 1 | 1 | 66.9 | 66.5 |
| 42 | 8 | 1 | 2 | 70.9 | 73.2 |
| 43 | 9 | 1 | 1 | 65.3 | 68.9 |
| 44 | II-2 | 1 | 1 | 72.9 | 70.3 |
| 45 | 10 | 1 | 1 | 70.8 | 70.8 |
| 46 | 11 | 1 | 1 | 71.8 | 73.1 |
| 47 | — | — | — | — | — |
| 48 | — | — | — | — | — |
| 49 | 12 | 1 | 1 | 69.6 | 71.9 |
| 50 | q | 1 | 1 | 69.7 | 69.9 |
| 51 | r | 1 | 2 | 64.4 | 66.8 |
| 52 | — | — | — | — | — |
| 53 | — | — | — | — | — |
| 54 | VII-2 | 6 | 6 | 63.3 | 66.2 |
| 55 | X-1 | 6 | 6 | 66.0 | 66.0 |
| 56 | IX | 6 | 6 | 63.4 | 60.6 |
| 57 | X-3 | 6 | 6 | 70.1 | 62.3 |
| 58 | VI-1 | 6 | 6 | 70.9 | 65.6 |
| 59 | X-2 | 6 | 6 | 69.6 | 66.1 |
| 60 | VI-2 | 6 | 6 | 67.1 | 67.8 |
| 61 | VII-1 | 6 | 6 | 66.3 | 66.2 |
| 62 | X-1 | 5 | — | 66.1 | — |
| 63 | IX | 4 | — | 63.0 | — |
| 64 | IX | 7 | — | 62.9 | — |
| 65 | IX | 6 | 8 | 58.6 | 62.2 |
| 66 | VII-1 | 4 | 8 | 68.4 | 67.1 |
| 67 | VI-2 | 4 | 8 | 67.8 | 69.0 |
| 68 | X-2 | 4 | 8 | 65.8 | 67.7 |
| 69 | VI-1 | 4 | 8 | 70.9 | 62.4 |
| 70 | X-1 | 4 | 8 | 66.8 | 68.9 |
| 71 | VII-2 | 4 | 8 | 68.2 | 66.9 |
| 72 | XXVII-3 | 6 | 6 | 74.4 | 77.1 |
| 73 | XXI | 4 | 8 | 73.7 | 77.3 |
| 74 | XXV-2 | 6 | 6 | 70.7 | 73.2 |
| 75 | XXV-4 | 6 | 6 | 73.0 | 80.6 |
| 76 | XXIV | 6 | 6 | 79.2 | 81.4 |
| 77 | XXIV | 6 | 6 | 79.2 | 75.5 |
| 78 | XXI | 6 | 6 | 69.4 | 68.2 |
| 79 | XXIII-1 | 6 | 6 | 75.7 | 77.2 |
| 80 | XXVII-1 | 6 | 6 | 78.0 | 72.5 |
| 81 | XX-2 | 6 | 6 | 69.3 | 73.1 |
| 82 | XXIII-2 | 6 | 6 | 71.7 | 71.2 |
| 83 | XXV-3 | 6 | 6 | 70.0 | 87.1 |
| 84 | XXVII-2 | 6 | 6 | 76.0* | 76.1 |
| 85 | XI | 6 | 6 | 64.6* | 64.6 |
| 86 | XVI-1 | 6 | 6 | 72.0* | 72.0 |
| 87 | XII | 6 | 6 | 68.1 | 67.7 |
| 88 | XI | 4 | 8 | 64.6 | 66.0 |
| 89 | XII | 4 | 8 | 66.8 | 67.0 |
| 90 | XVI-2 | 6 | 6 | 65.2 | 69.8 |
| 91 | XV-2 | 6 | 6 | 67.2 | 71.8 |
| 92 | XV-1 | 6 | 6 | 73.3 | 71.7 |
| 93 | XIV-4 | 6 | 6 | 75.0 | 78.0 |
| 94 | XIII-1 | 6 | 6 | 74.8 | 72.4 |
| 95 | XIII-2 | 6 | 6 | 75.8 | 75.0 |
| 96 | XIV-2 | 6 | 6 | 76.0 | 79.1 |
| 97 | XIV-3 | 6 | 6 | 74.0 | 74.2 |
| 98 | XXX-2 | 6 | 6 | 76.6 | 81.0 |
| 99 | XVII-2 | 6 | 6 | 73.1 | 77.4 |
| 100 | XXII | 6 | 6 | 63.9 | 73.6 |
| 101 | XXXI | 6 | 6 | 72.9 | 77.1 |
| 102 | XXX-1 | 6 | 6 | 73.3 | 74.9 |
| 103 | XXIX | 6 | 6 | 77.1 | 78.7 |
| 104 | XXVI | 6 | 6 | 72.2 | 73.0 |
| 105 | XIX | 6 | 6 | 70.8 | 69.3 |
| 106 | XVIII | 6 | 6 | 71.8 | 72.3 |
| 107 | XXVIII | 6 | 6 | 71.1 | 72.6 |
| 108 | XVII-1 | 6 | 6 | 66.7 | 64.1 |
| 109 | 14 | 4 | 6 | 67.2 | 70.0 |
| 110 | 13 | 6 | 6 | 66.6 | 69.0 |
| 111 | A | 6 | 6 | 69.4 | 72.4 |
| 112 | — | — | — | — | — |
| 113 | — | — | — | — | — |
| 114 | — | — | — | — | — |
| 115 | XXXIII | 6 | 6 | 58.8 | 58.2 |
| 116 | XXXII | 6 | 6 | 70.9 | 71.7 |

The amine and peroxide pastes are loaded with filler on separate, large porcelain tile plates (16×16 cm). Two large porcelain spatulas (3 cm wide) are used to mix in the frit filler. One spatula is used to clean off the other in the mixing. Mixing is accomplished by a mashing motion. A least 75 and 87 wt% frit can be introduced into the amine and peroxide pastes, respectively. With proper elimination of extreme fines without reducing strength more filler can be introduced into the pastes. Coarse particles are mixed into the pastes before the finer sized fractions are added.

In all specimen preparations, approximately equal volumes of the amine and peroxide containing pastes were mixed. Filler contents did not attain the levels of commercial products because no attempt was made to optimize filler particle size and viscosity relationships.

Volume percentages of resin in the mixed paste and of resin and filler in the test specimens were calculated from determined densities, specimen weights and specimen volumes. No ashing techniques were used and volumes of prepared specimens were determined hydrostatically. Small bars of pure polymerized resin were prepared bubble-free by the application of slight pressure during setting. Volumes of these bars were measured hydrostatically. The average density calculated from these measurements was 1.197 gm/ml. This value was used in making the calculations of resin volume percentages in the specimens.

A large number of additional resin mixtures were prepared to test the function of various catalyst concentrations in the ratio of BIS-GMA to TEGDMA, 70% to 30%, resin base. The formulations are set forth in Table 1. A number of sol compositions and frit compositions were also prepared and tested in the final product. These compositions are set out in Tables II and III respectively. Table IV sets forth a listing of the frit calcination conditions for the various frit compositions. These tables represent some of the many additional and alternative formulations and procedures which are encompassed within this invention.

Tables X through XIX refer to various properties for which the frits and product specimens were tested and compared. Reference will be made to these tables throughout the remainder of the specification.

TESTING OF SPECIMENS

All test specimens were formed by mixing predetermined weights of the amine paste and the benzoyl peroxide paste. After mixing the mixture was then placed into an appropriate mount or mold.

(a) Setting contraction.—No mold was used to make specimens for setting contraction measurements. An amount of mixed paste, approximately 0.7 gm was suspended on a platinum hook in distilled water at either room temperature ($22° \pm 1°$ C.) or at an elevated temperature within a range of 42° to 35° C. (Table X). Changes in volume were determined hydrostatically from 1.5 to 30 minutes after the start of mixing.

Hydrostatic measurements were made on a balance accurate to 0.1 mg. The weight of the wire and test material in distilled water was monitored from the time of immersion. From the increase in the weight of the test specimen while immersed in water and the weight of the material dry, the percent volume setting contraction was calculated by the formula:

Contraction vol. $\% = \Delta V/V \times 100$

Volumes were calculated using the density of water at various monitored temperatures of measurement. Absorption of water during the course of experimentation appeared to be negligible, that is, within the margin of error of the experimental technique.

In the elevated temperature measurements the bath was protected from quick heat loss by styrofoam insulation and a mineral oil film on the bath surface to retard evaporation. Distilled water was heated on a hot plate before emplacement and was changed between the measurements.

(b) Translucency.—No mold was used to form the translucency specimens. The mixed paste was placed between two lightly oiled 4×5 inch photographic glass plates. These glass plates were separated by two one mm thick glass microscope slides which were placed at opposing corners of the bottom glass plate. Amounts of amine and peroxide catalyzed pastes which were mixed together varied from 1.5 to 2.4 gm.

The mixed paste was placed on the bottom plate and flattened into a disc $1 \pm 0.025$ mm with the top plate. Length of the top plate was at right angles to that of the bottom plate. A weight was placed on top of the glass plate and left until the plate had hardened. The glass plates with the sandwich resin remained in position at room temperature for up to 17 hours. Resin mixes which had prolonged setting times had to remain under the glass plates in order to obtain a smooth surface when pulled apart.

After removal of the resin wafer, oil was wiped off as completely as possible with absorbent paper. Resin wafers were stored in distilled water at $37° \pm 1°$ C. for 27-119 days. Translucencies were determined after prolonged aging in water. Equilibrium water pickup appear essentially to have been obtained in all cases. Values were obtained by visual comparison of the translucency specimen with standards against a variegated black and white background according to American

TABLE X

Setting Contraction[a]

| Filler | Designation Mix No. | Setting Time, Min. 22±1° C. | Resin in Mixed Paste, Vol % (Range) Exclusive of Voids | Setting Contraction at Room Temperature, 22±1° C. $t_c = 1.5_{min.}$ to $t_{final} = 30.0$ | | | | Setting Contraction, Elevated Temperature $t_o = 1.5_{min.}$ to $t_{final} = 30.0_{min.}$ | | | | | | Flexure Strength kg/cm² | |
|---|---|---|---|---|---|---|---|---|---|---|---|---|---|---|---|
| | | | | n | Mean, Vol % | Std Deviation | Std Error of Mean at 95% | n | Temperature ± 1° C. (Mean) | | Setting Contraction | | | | |
| | | | | | | | | | $t_o = 1.5$ min. | $t = 30.0$ min. | Mean, Vol % | Std Deviation | Std Error of Mean at 95% | Mean | Std Error of Mean at 95% |
| Adaptic | — | 3¼ | 39.0 | 2 | 1.80 | 0.085 | ±0.76 | 1 | 39.0 | 35.0 | 2.40 | — | — | 906.5 | ±65.7 |
| Prestige | — | 5 | n.d.[b] | 1 | 2.56 | — | — | 1 | 38.8 | 35.2 | 3.22 | — | — | 721.3 | ±59.3 |
| A (Corning Glass 1720) | 111 | 2¼ | 46.6 | 1 | 2.53 | — | — | — | — | — | — | — | — | 858.6 | ±61.0 |
| X-1 | 70 | 4¼ | 50.0–50.2 | 3 | 2.40 | 0.112 | ±0.28 | 1 | 39.2 | 35.6 | 2.78 | — | — | 663.6 | ±179.3 |
| XIV-2 | 96 | 2¼ | 42.2 | 1 | 2.50 | — | — | — | — | — | — | — | — | 845.3 | ±106.8 |
| XII | 89 | 3¼ | 51.2 | 1 | 2.70 | — | — | 3 | 39.4 | 35.6 | 2.95 | 0.151 | ±0.38 | 602.6 | ±13.1 |
| XXII | 100 | 4 | 49.5–50.4 | 2 | 2.99 | 0.346 | very large | 2 | 39.4 | 35.5 | 3.44 | 0.276 | very large | 719.4 | ±21.6 |
| XXVI | 104 | 2¼ | 44.65 | 1 | 2.45 | — | — | 1 | 38.8 | 35.5 | 3.71 | — | — | 641.4 | ±68.9 |
| XXVIII | 107 | 3¼ | 44.85 | 1 | 3.28 | — | — | — | — | — | — | — | — | 773.1 | ±91.6 |
| 13-[XVII-1] A, L 67.8% | 110 | 5¼ | 50.5– | 6 | 2.68 | 0.156 | ±0.16 | 3 | 39.7 | 36.0 | 3.36 | 0.214 | ±0.53 | 957.1 | ±20.6 |

[a]None of filler products tested had +200 mesh particles.
[b]Not determined.

Dental Association Specification No. 9 for Silicate Cements.

(c) Setting time.—Determination of setting time was made during the preparation of translucency specimens. A slide immobilization test was used. The test was applied at room temperature (22°±1° C.) and 50–55% humidity, the humidity used for all room temperature specimen preparations. To make the test, a slight rotational movement of the top glass photographic plate with respect to the bottom plate was applied manually. Termination of the ability to make this rotational movement determined the setting time (Table XI).

TABLE XI

| | | | Translucency Specimens | | | Water Pickup[b] | | |
|---|---|---|---|---|---|---|---|---|
| Designation | | | Resin Mixed Paste Mean Vol. % | Opacity $C_{0.70}$ × $10^{-2}$ | Setting Time min. (22°±1° C.) | n | gm $H_2O$/ml Specimen | Aging, Days in Dist. $H_2O$ (30:1-$C^2$) | n |
| General Type of Filler | Filler | Mix | | | | | | | |
| Commercial (Single Component) | A | 8 | 46.8 | 35 | 1¼–1[a] | 2 | 0.0341 | 114 | 1 |
| | A | 111 | 46.6 | <35 | 2¼ | 1 | 0.0266 | 69 | 1 |
| | B | 3 | 38.4 | >55 | n.d.[a] | — | n.d. | 115 | 1 |
| | D | 2 | 39.7 | 35–40 | 1¼–1½ | 2 | n.d. | 118–119 | 2 |
| | F | 12 | 42.2 | <35 | 2 | 1 | n.d. | 119 | 1 |
| | G | 13 | 41.3 | 35–40 | 2 | 2 | n.d. | 118 | 2 |
| | H | 15 | 39.4 | 40 | 1° | 1 | n.d. | 118 | 2 |
| | I | 16 | 39.8 | 40–45 | 2½ | 1 | n.d. | 114 | 1 |
| Experimental Frit | I | 5 | 47.6 | 45–50 | 3½ | 1 | n.d. | 114 | 1 |
| | II-1 | 14 | 44.5 | 45 | 2½ | 1 | 0.1095 | 113 | 1 |
| | II-2 | 10 | 56.3 | 45 | 2½ | 1 | 0.0630 | 113 | 1 |
| | II-2 | 44 | 47.7 | 45 | 2½ | 1 | n.d. | 113 | 1 |
| | II-3 | 11 | 47.0 | 40–45 | 2½ | 1 | n.d. | 115 | 1 |
| | II-3 | 62,55 | 52.2 | 45 | 5 | 1 | n.d. | 114 | 1 |
| | III | 9 | 43.2 | 40–45 | 3 | 1 | n.d. | 113 | 1 |
| | IV | 7 | 54.5 | n.d.[a] | 11 | 1 | n.d. | — | — |
| | V | 6 | 46.4 | 45–50 | 4 | 1 | n.d. | 115 | 1 |
| | VI-1 | 69 | 51.6 | 40–45 | 2 | 1 | n.d. | 105 | 1 |
| | VI-2 | 67 | 52.4 | 45 | 2½ | 1 | 0.0561 | 105 | 1 |
| | VII-1 | 66 | 49.7 | 50–55 | 2 | 1 | 0.0678 | 103 | 1 |
| | VII-1 | 61 | 51.3 | n.d. | 2½ | 1 | 0.0664 | 113 | 1 |
| | VII-2 | 71 | 49.9 | 55 | 2½ | 1 | n.d. | 105 | 1 |
| | IX | 65,56 | 59.6 | >55 | 1½ | 1 | 0.0425 | 113 | 1 |
| | IX | 65,63 | 56.4 | 50–55 | 3½ | 1 | n.d. | 105 | 1 |
| | X-1 | 70 | 50.0 | 40–45 | 4½ | 1 | 0.0591 | 105 | 1 |
| | X-2 | 68 | 52.2 | 40–45 | 2½ | 1 | n.d. | 105 | 1 |
| | XI | 85 | 53.5 | 55 | 5 | 1 | n.d. | 93 | 1 |
| | XI | 88 | 52.8 | 55 | 3 | 1 | n.d. | 93 | 1 |
| | XII | 87 | 50.1 | 45 | 8-1/6 | 1 | n.d. | 93 | 1 |
| | XII | 89 | 51.2 | 45–50 | 3½ | 1 | 0.0988 | 93 | 1 |
| | XIII-1 | 94 | 44.8 | 50 | 2½ | 1 | 0.0255 | 90 | 1 |
| | XIII-2 | 95 | 43.3 | 50 | 3 | 1 | 0.0253 | 89 | 1 |
| | XIV-2 | 96 | 42.2 | 45–50 | 2½ | 1 | 0.0473 | 89 | 1 |
| | XIV-3 | 97 | 47.9 | 55 | 2½ | 1 | n.d. | 89 | 1 |
| | XIV-4 | 93 | 41.7 | 45 | 2½ | 1 | n.d. | 91 | 1 |
| | XV-1 | 92 | 45.5 | 45–50 | 7½ | 1 | n.d. | 91 | 1 |
| | XV-2 | 91 | 48.7 | n.d. | 6½ | 1 | n.d. | 91 | 1 |
| | XVI-1 | 86 | 46.2 | 40–45 | 2½ | 1 | 0.0276 | 93 | 1 |
| | XVI-2 | 90 | 51.8 | 45 | 3-1/6 | 1 | n.d. | 91 | 1 |
| | XVII-1 | 108 | 54.2 | 45 | 5½ | 1 | n.d. | 72 | 1 |
| | XVII-2 | 99 | 45.3 | 50–55 | 1½ | 1 | n.d. | 76 | 1 |
| | XVIII | 106 | 47.7 | 45–50 | 4 | 1 | n.d. | 72 | 1 |
| | XIX | 105 | 48.8 | 50–55 | 15½ | 1 | 0.0609 | 72 | 1 |
| | XX-1 | 78 | 51.1 | 55 | 4½ | 1 | n.d. | 98 | 1 |
| | XX-2 | 81 | 48.2 | 55 | 3½ | 1 | n.d. | 98 | 1 |
| | XXI | 73 | 40.9 | n.d. | 5/6 | 1 | n.d. | — | — |
| | XXII | 100 | 49.5 | 45–50 | 4 | 1 | 0.0339 | 76 | 1 |
| | XXIII-1 | 79 | 42.1 | 50–55 | 3½ | 1 | n.d. | 98 | 1 |
| | XXIII-2 | 82 | 48.6 | 50–55 | 2½ | 1 | n.d. | 96 | 1 |
| | XXIV | 76 | 39.0 | 50–55 | 3½ | 1 | n.d. | 99 | 1 |
| | XXIV | 77 | 43.3 | 50–55 | 4½ | 1 | n.d. | 98 | 1 |
| | XXV-1 | 75 | 41.3 | 50–55 | 3½ | 1 | n.d. | 99 | 1 |
| | XXV-2 | 74 | 48.8 | 50 | 2½ | 1 | n.d. | 99 | 1 |
| | XXV-3 | 83 | 38.8 | 45–50 | 2½ | 1 | n.d. | 96 | 1 |
| | XXVI | 104 | 44.7 | 50 | 2½ | 1 | n.d. | 75 | 1 |
| | XXVII-1 | 80 | 43.1 | 50–55 | 4½ | 1 | 0.0298 | 98 | 1 |
| | XXVII-2 | 84 | 42.4 | 45–50 | 2 | 1 | 0.0238 | 96 | 1 |
| | XVII-3 | 72 | 43.9 | 50–55 | 4 | 1 | 0.0246 | 100 | 1 |
| | XXVIII | 107 | 44.9 | 50 | 3½ | 1 | 0.0473 | 72 | 1 |
| | XXIX | 103 | 41.7 | 50–55 | 3 | 1 | 0.0181 | 75 | 1 |
| | XXX-1 | 102 | 44.0 | 45 | 2½ | 1 | 0.0351 | 76 | 1 |
| | XXX-2 | 98 | 39.1 | 55 | 2 | 1 | n.d. | 78 | 1 |
| | XXXI | 101 | 39.7 | 40–45 | 3½ | 1 | 0.0649 | 76 | 1 |
| | XXXII | 116 | 48.0 | 55 | 2½ | 1 | 0.0337 | 27 | 1 |
| | XXXIII | 115 | 62.4 | 40–45 | 9 | 1 | 0.0289 | 27 | 1 |
| Commercial | a | 19 | 38.2 | >55 | 5/6–1½ | 2 | n.d. | 115 | 1 |
| | b | 20 | 40.2 | >55 | 1½ | 1 | 0.0174 | 115 | 1 |

TABLE XI-continued

Translucency Specimens

| Designation | | | | | | Water Pickup[b] | | |
|---|---|---|---|---|---|---|---|---|
| General Type of Filler | Filler | Mix | Resin Mixed Paste Mean Vol. % | Opacity $C_{0.70} \times 10^{-2}$ | Setting Time min. (22°± 1° C.) | n | gm $H_2O$/ml Specimen | Aging, Days in Dist. $H_2O$ (30:1-$C^2$) | n |
| (Multi- | c | 21 | 43.4 | 55 | 1½ | 1 | n.d. | 115 | 1 |
| Com- | d | 22 | 36.2 | 50–55 | 1½ | 1 | n.d. | 115 | 1 |
| ponents | e | 23 | 38.3 | 55 | 1½ | 1 | n.d. | 115 | 1 |
| or | f | 24 | 43.3 | 35–40 | 1½ | 1 | n.d. | 119 | 1 |
| Blends | h | 26 | 45.2 | 35–40 | 1½ | 1 | n.d. | 118 | 1 |
| | i | 27 | 44.3 | 50–55 | n.d. | — | n.d. | 118 | 1 |
| | j | 28 | 46.6 | 50–55 | 2 | 1 | n.d. | 118 | 2 |
| | k | 29 | 40.6 | 40–45 | 1½ | 1 | n.d. | 118 | 1 |
| | p | 34 | 50.3 | n.d. | n.d. | — | n.d. | — | — |
| | q | 50 | 47.9 | 40 | 1½ | 2 | n.d. | 115 | 2 |
| | r | 51 | 52.5 | 40 | 1½ | 1 | n.d. | 118 | 1 |
| Commer- | 1 | 35 | 47.8 | 40–45 | 2 | 1 | n.d. | 118 | 1 |
| cial | 5 | 39 | 45.4 | 45 | 3 | 1 | n.d. | 115 | 1 |
| and | 8 | 42 | 46.6 | 40–45 | 2 | 1 | n.d. | 118 | 1 |
| Experi- | 9 | 43 | 52.0 | 35–40 | 5½ | 1 | 0.0577 | 118 | 1 |
| mental | 10 | 45 | 49.3 | 35–40 | 2 | 1 | n.d. | 118 | 1 |
| Frit | 11 | 46 | 46.2 | 40 | 1½ | 1 | n.d. | 115 | 1 |
| Blends | 12 | 49 | 46.8 | 40–45 | n.d. | — | n.d. | 114 | 1 |
| | 13 | 110 | 50.5 | 40–45 | 5½ | 1 | 0.0390 | 69 | 1 |
| | 14 | 109 | 50.0 | 45–50 | 1½ | 1 | 0.0465 | 69 | 1 |

[a]Not determined.
[b]Specimens after aging used for translucency determination.
NOTE: Translucencies of Adaptic, Coamic and Prestige were not determined.

(d) Thermal expansion.—Specimens for thermal expansion were prepared from stainless steel molds which produced specimens 5 mm in diameter and 4.5 mm in height. Mixed paste was placed in the mold, tamped down with a Teflon dowel and covered with a weighted microscope slide. Then the mold assembly was transferred within 1¼ min. after start of mixing to a 37° C. 100% humidity oven for approximately 15 minutes. Upon ejection from the mold, specimens were weighed and then stored in distilled water at 37°±1° C. for 16 to 18 days and at 22°±1° C. for one day before testing.

Thermal expansions were measured with a microquartz rod assembly with a linear heating rate of 1° C./1½ min. Temperature changes were accomplished by means of a water bath (Table XII).

TABLE XII

Thermal Expansion

| Filler | Mix No. | Specimen No. | Resin in Mixed Paste, Vol % | Aging, Days in Distilled Water, 37 ± 1° C.[a] | Thermal Expansion 10°–65° C. (Heating Rate Approx. 1° C./1½ min.) ±1 × $10^{-6}$/°C. |
|---|---|---|---|---|---|
| XIV-2 | 96 | 503 | 42.2 | 17½ | 27.2 × $10^{-6}$/°C. |
| XXII | 100 | 513 | 50.5 | 16½ | 31.8 × $10^{-6}$/°C. |
| Adaptic | — | — | 39.0 | 14 | 32.0 × $10^{-6}$/°C. |

[a]Aged one day at room temperature, 22° ± 1° C., before making test.

(e) Microhardness.—In the making of specimens for Knoop microhardness two different molds were used. One was a cylinder with a cylindrical plunger in which specimens 13 mm in diameter and 15 mm in length were prepared. Upon placement they were weighted down with a glass slide and set at 22°±1° C. The other mold used was a cup with an inner diameter of 22.9 mm and a depth of 11.4 mm. Mixed pastes were set in these molds at 22°±1° C. under a glass slide in distilled water. The glass slide was removed while the filled cup was still in the water.

All prepared specimens were stored in distilled water at 37°±1° C. for 85 to 141 days and aged one day at 22°±1° C. before testing (Table XIII). Tests were made with a Kentron microhardness tester from Ken Cliff Laboratories, Peekskill, New York having a Knoop diamond point and a 100 gram load.

TABLE XIII

| Specimen Description | | | | | Knoop Hardness 100g Load[a] | | | Filler Sieve Size | |
|---|---|---|---|---|---|---|---|---|---|
| Filler | Mix[b] No. | Specimen No. | Resin in Mixed Paste Vol. % | Aging, Days in Dist. $H_2O$ 37 ± 1° C. | n | Knoop Hardness Mean kg/mm² | Std Error of Mean at 95% | Std Deviation | Vol. % +200 Mesh | Vol. % −400 Mesh |
| VI-1 | 69 | 208 | 52.3 | 141 | 16 | 36.91 | ±2.51 | 4.71 | 13.5 | 52.4 |
| VI-2 | 67 | 207 | 52.4 | 141 | 20 | 26.93 | ±3.06 | 6.53 | 8.8 | 52.7 |
| XII | 89 | 631 | 51.2 | 83 | 6 | 34.66 | ±2.94 | 2.80 | — | 47.4 |

TABLE XIII-continued

Knoop Hardness 100g Load[a]

| Filler | Mix[b] No. | Specimen No. | Resin in Mixed Paste Vol. % | Aging, Days in Dist. H$_2$O 37 ± 1° C. | n | Knoop Hardness Mean kg/mm$^2$ | Std Error of Mean at 95% | Std Deviation | Filler Sieve Size Vol. % +200 Mesh | Filler Sieve Size Vol. % −400 Mesh |
|---|---|---|---|---|---|---|---|---|---|---|
| XIV-2 | 96 | 626 | 42.2 | 85 | 10 | 44.84 | ±2.38 | 3.33 | — | 94.8 |
| XVIII | 106 | 634 | 47.7 | 83 | 6 | 37.45 | ±0.98 | 0.93 | — | 92.6 |
| XXII | 100 | 627 | 49.8 | 85 | 20 | 28.69 | ±1.67 | 3.57 | — | 58.9 |
| XXVIII | 107 | 635 | 44.8 | 83 | 11 | 41.39 | ±3.89 | 5.79 | — | 92.7 |
| XXIX | 103 | 633 | 41.8 | 83 | 16 | 40.16 | ±4.08 | 7.66 | 12.4 | 47.5 |
| XXX-1 | 102 | 632 | 44.0 | 83 | 12 | 34.55 | ±4.28 | 6.73 | 8.6 | 47.9 |
| 13-[XVII-1] A,L 67.8% | 110 | 628 | 50.5 | 85 | 10 | 32.47 | ±4.28 | 5.99 | | 91.8 |
| 14-[XIX], A,L 68.2% | 109 | 630 | 50.1 | 85 | 16 | 40.16 | ±4.08 | 7.66 | 14.4 | 57.3 |
| Adaptic | — | 667 | 39.0 | 85 | 6 | 49.22 | ±3.92 | 3.73 | n.d. | n.d. |
| Prestige | — | 629 | n.d.[c] | 85 | 16 | 38.28 | ±2.43 | 4.57 | n.d. | n.d. |
| Prestige | — | 665 | n.d. | 85 | 12 | 43.42 | ±4.35 | 6.84 | n.d. | n.d. |

[a] Aged one day at 22 ± 1° C. before making test.
[b] From Table IX
[c] Not determined.

(f) Modulus of elasticity.—Molds and procedures used in the preparation of specimens for modulus of elasticity determinations were those recommended in the American Dental Association test for silicate cements. Cylindrical test specimens were prepared with a diameter of approximately 6 mm and a height of 11.95±0.10 mm. Approximately 1½ minutes after the start of mixing, filled molds were transferred to a 37°±1° C., 100% humidity oven for 15 minutes.

Ejected specimens were stored in distilled water at 37°±1° C. for 87–101 days and aged one day in distilled water at 22°±1° C. before testing (Table XIV). A crosshead speed of 0.5″/min. was applied directly to the prepared cylinders on an Instron testing machine. A chart speed of 2″/min. was used. Tests were made while the specimens were wet after excess water had been blotted off. Dimensions of all specimens were measured accurately with a toolmaker's microscope.

TABLE XIV

Modulus of Elasticity by Compression

| Order of Strength Modulus | Filler | Mix. No. | Resin in Mixed Paste Vol. % Mean | n[c] | Aging,[a] Days in Distilled Water, 37 ± 1° C. | Water pickup, gm/ml of Specimen | Modulus of Elasticity[d] Mean, × 10$^4$ kg/cm$^2$ | Std. Error of Mean 95% × 10$^4$ kg/cm$^2$ | Std. Deviation × 10$^4$ kg/cm$^2$ | Size Vol. % Filler +200 mesh |
|---|---|---|---|---|---|---|---|---|---|---|
| 1 | Adaptic | 39.0 | — | 3 | 87–96 | 0.0097 −0.0110 | 8.84 | ±0.46 | 0.184 | n.d. |
| 2 | XIV-2 | 96 | 42.2 | 1 | 88 | 0.0315 | 8.21 | — | — | — |
| 3 | XIII-2 | 95 | 43.25 | 2 | 88 | 0.0175 −0.0182 | 8.03 | ±2.44 | 0.271 | — |
| 4 | V | 6 | 46.4 | 1 | 101 | n.d. | 7.95 | — | — | — |
| 5 | XIII-1 | 94 | 44.8 | 3 | 88 | 0.0183 −0.0204 | 7.67 | ±0.90 | 0.362 | — |
| 6 | XIV-4 | 93 | 41.7 | 1 | 89 | 0.0286 | 7.51 | — | — | — |
| 7 | XXVII-1 | 80 | 43.2 | 1 | 91 | 0.0182 | 7.48 | — | — | 34.4 |
| 8 | XVI-2 | 90 | 51.7 | 1 | 89 | 0.0753 | 7.44 | — | — | 16.9 |
| 9 | XXV-4 | 75 | 41.6 | 1 | 94 | 0.0199 | 7.39 | — | — | — |
| 10[b] | XXIV | 76 | 39.0 | 4[b] | 91 | 0.0151 −0.0161 | 7.17[c] | ±0.35 | 0.140 | 27.0 |
| 11 | II-2 | 10 | 57.0 | 1 | 97 | 0.0452 | 7.02 | — | — | — |
| 12 | XX-2 | 81 | 48.1 | 1 | 90 | 0.0176 | 7.00 | — | — | — |
| 13 | XX-1 | 78 | 51.1 | 2 | 90–91 | 0.0221 −0.0247 | 6.97 | ±0.98 | 0.109 | — |
| 14 | XI | 88 | 52.9 | 1 | 89 | 0.0598 | 6.97 | — | — | — |
| 15 | I | 5 | 47.6 | 2 | 101 | n.d. | 6.94 | ±0.54 | 0.060 | — |
| 16 | X-2 | 68 | 52.0 | 1 | 95 | 0.0441 | 6.93 | — | — | — |
| 17 | XVI-1 | 86 | 46.2 | 2 | 89 | 0.0903 −0.0914 | 6.84 | ±1.09 | 0.122 | 16.5 |
| 18 | XII | 89 | 51.2 | 1 | 89 | 0.0668 | 6.79 | — | — | — |
| 19 | X-1 | 62, 55 | 52.2 | 1 | 96 | 0.0407 | 6.75 | — | — | — |
| 20 | X-1 | 70 | 50.1 | 1 | 94 | 0.0428 | 6.70 | — | — | — |
| 21 | XI | 85 | 53.5 | 3 | 90 | 0.0623 −0.0626 | 6.27 | ±1.49 | 0.601 | — |
| 22 | VI-1 | 69 | 51.9 | 1 | 95 | 0.0482 | 6.27 | — | — | 13.5 |
| 23 | IX | 65, 56 | 59.6 | 1 | 96 | n.d. | 6.10 | — | — | 83.0 |

TABLE XIV-continued

Modulus of Elasticity by Compression

| | | Specimen Description | | | | Modulus of Elasticity[d] | | | |
|---|---|---|---|---|---|---|---|---|---|
| Order of Strength Modulus | Filler | Mix. No. | Resin in Mixed Paste Vol. % Mean | n[c] | Aging,[a] Days in Distilled Water, 37 ± 1° C. | Water pickup, gm/ml of Specimen | Mean, × 10⁴ kg/cm² | Std. Error of Mean 95% × 10⁴ kg/cm² | Std. Deviation × 10⁴ kg/cm² | Size Vol. % Filler +200 mesh |
| 24 | XXIV | 77 | 43.3 | 2 | 91–94 | 0.0169–0.0378 | 5.83 | ±5.90 | 0.657 | 27.0 |
| 25 | IX | 63, 65 | 56.5 | 1 | 95 | 0.0438 | 5.79 | — | — | 83.0 |
| 26 | A.Corning Glass Beads | 8 | 46.9 | 1 | 101 | 0.0193 | 5.77 | — | — | — |
| 27 | VI-2 | 67 | 52.4 | 1 | 95 | 0.0471 | 5.70 | — | — | 8.8 |

[a]Aged one day in distilled water at room temperature, 22 ± 1° C. before testing.
[b]Rejection of one specimen by outlier test for modulus of elasticity.
[c]n = 3.
[d]Load rate = 0.5 in/min in Instron. One kg force/cm² = 9.806650 Pa (g) Tensile strength.—Diametrical tensile strength was measured on cylindrical specimens with a diameter of 5.97±0.01 mm and a thickness of 3.15±0.01 mm. These specimens were prepared in a hardened steel mold.

Mixed paste was tamped down into the steel mold cavity which was bottomed with a flattened steel plunger. The upper surface was pressed down with a glass slide. A 50 gm weight was put on the slide and the filled mold was transferred to a 37°±1° C., 100% humidity oven for 15 minutes. Upon ejection from the mold, the specimen was weighed and stored in distilled water at 37°±1° C. for 56–59 days (Table XV). All specimens were aged one day at 22°±1° C. in distilled water before testing.

(h) Flexure modulus.—Bar flexure modulus specimens were made in a hardened steel split mold. Specimens were prepared 19.83 mm long, 2.55 mm wide, and 1.75 mm thick. The mold cavity was bottomed by a steel piston. Top surfaces were formed by a weighted microscope slide. Approximate setting times were determined for the individual specimen preparations by noting the time from start of mixing required to immobilize the covering glass slide to a lengthwise manual motion. Specimen dimensions were determined before testing with a precision micrometer.

The specimens were prepared at 22°±1° C. and a relative humidity of 50–55%. They were kept under the glass plate in the mold cavity 6–10 minutes or longer depending on the setting time. After the specimens were

TABLE XV

Diametrical Tensile Strength
(37 ± 1° C., 100% Humidity Set)

| Filler | Mix No. | n | Resin in Mixed Paste, Vol. % Mean | Range | Aging,[a] Days in Distilled Water 37 ± 1° C. | Water Pickup, gm/ml of Specimen | Tensile Strength[b] kg/cm² Mean | Std Error of Mean at 95% | Std Deviation | Coefficient of Variation % |
|---|---|---|---|---|---|---|---|---|---|---|
| Adaptic | — | 4 | n.d. | n.d. | 56 | 0.0098–0.0116 | 362 | ±64 | 40 | 11.0 |
| XXVIII | 107 | 12 | 44.8 | 44.8–44.9 | 57–58 | 0.0191–0.0212 | 332 | ±23 | 36 | 11.0 |
| XXVI | 104 | 8 | 44.7 | 44.6–44.8 | 58–59 | 0.0285–0.0314 | 312 | ±20 | 24 | 7.6 |

[a]Aged one day at 22 ± 1° C. before testing
[b]One kg-force/cm² = 9.806650 Pa; crosshead speed = 1 cm/min. Instron.

Individual specimen dimensions were measured accurately before testing with the toolmaker's microscope. Tests were made with the Instron and a crosshead speed of 1 cm/min. All specimens were tested immediately after removal from the distilled water after excess water had been blotted off. No platens were used.

extracted, mold lubricant was wiped off with absorbent paper. They were placed vertically lengthwise in a small vial filled with distilled water and placed in a 37°±1° C. oven for two weeks to four months (Table XVI). Specimens were aged two to three days at 22°±1° C. before breaking.

TABLE XVI

Flexure Strength (Three Point)

| Category | Filler Type | Mix No. | n | Resin in Mixed Paste, Vol.% (Bar) Mean | Range | Aging, Days in Distilled Water 37±1° C. | Water Pickup, gm/ml, Mean (on Specimen) | Opacity$^a$ C$_{0.70}$ x10$^{-2}$ | Approx. Setting Time, min. 22±1° C. 50-55% Humidity (max) | Flexure Strength kg/cm$^2$ Mean | Std Error of Mean at 95% | Std Deviation |
|---|---|---|---|---|---|---|---|---|---|---|---|---|
| Controls Commercial Products | Product T | — | 11 | 39.0 | — | 60–117 | 0.0194 | n.d. | 3½ | 907 | ±66 | 98 |
| | Product Z$^b$ | — | 6 | — | — | 16 | 0.0130 | n.d. | 2½ | 879 | ±67 | 64 |
| | Product X | — | 6 | — | — | 15–16 | 0.0137 | n.d. | 5 | 721 | ±59 | 57 |
| Commercial Filler, Experimental Product | A (Corning glass beads, 1720, -325 mesh) | 8 | 7 | 46.8 | 46.6–47.0 | 108–140 | 0.0310 | 35 | 1½ | 927 | ±41 | 45 |
| | XIV-4 | 111 | 6 | 46.6 | 46.5–46.7 | 63–70 | 0.0260 | <35 | 3 | 859 | ±61 | 58 |
| | XIV-4 | 93 | 3 | 41.7 | 41.6–41.8 | 94–96 | n.d. | 45 | 2½ | 900 | ±49 | 20 |
| | XIII-1 | 94 | 3 | 44.9 | 44.8–45.0 | 94–98 | 0.0249 | 50 | 3 | 896 | ±106 | 43 |
| | XIV-2 | 96 | 3 | 42.2 | 42.2–42.2 | 94–98 | 0.0490 | 45–50 | 3 | 845 | ±107 | 43 |
| | X-2 | 68 | 3 | 52.3 | 52.1–52.4 | 100–107 | 0.0607 | 40–45 | 2½ | 806 | −129 | 52 |
| | II-2 | 10 | 6 | 56.7 | 56.6–56.8 | 107–134 | 0.0629 | 45 | 2½ | 774 | ±98 | 93 |
| | XXVIII | 107 | 6 | 44.85 | 44.8–44.9 | 66–87 | 0.0239 | 50 | 3½ | 773 | ±92 | 87 |
| | III | 14 | 5 | 44.2 | 43.8–44.6 | 112–134 | 0.1134 | 45 | 2½ | 763 | ±113 | 91 |
| | XVIII | 106 | 7 | 47.7 | 47.7–47.7 | 66–73 | 0.0230 | 45–50 | 4 | 758 | ±25 | 27 |
| | V | 6 | 5 | 46.45 | 46.4–46.5 | 107–134 | 0.0220 | 45–50 | 4 | 752 | ±181 | 146 |
| Good Trans lucency | IX | 44 | 5 | 47.8 | 47.7–47.9 | 108–135 | 0.0631 | 45 | 2½ | 748 | ±121 | 98 |
| | XXXIII | 115 | 6 | 62.4 | 62.4–62.4 | 19–27 | 0.0316 | 40–45 | 9½ | 741 | ±100 | 95 |
| Filler II-3 | XV-1 | 92 | 1 | 45.5 | — | 96 | 0.0691 | 45–50 | 7½ | 725 | — | — |
| | 11 | 6 | 47.0 | 46.8–47.2 | — | 0.0841 | 40–45 | 2½ | 724 | ±131 | 124 | |
| | XXIII | 100 | 7 | 50.0 | 49.5–50.4 | 69–79 | 0.0328 | 45–50 | 4½ | 719 | ±22 | 23 |
| | XXXI | 101 | 6 | 39.7 | 39.5–39.8 | 68–78 | 0.0565 | 40–45 | 3½ | 699 | ±40 | 38 |
| | 1 | 5 | 5 | 47.6 | 47.6–47.6 | 107–140 | 0.0311 | 45–50 | 3½ | 699 | ±127 | 102 |
| | X-1 | 70 | 3 | 50.1 | 50.0–50.2 | 103–106 | 0.0570 | 40–45 | 4½ | 664 | ±179 | 72 |
| | XVII-1 | 108 | 3 | 54.2 | 54.2–54.2 | 66–72 | 0.0485 | 45 | 5½ | 651 | ±43 | 176 |
| | XXVI | 104 | 6 | 44.65 | 44.6–44.7 | 66–74 | 0.0370 | 50 | 3 | 641 | ±69 | 66 |
| | VI-1 | 69 | 3 | 51.9 | 51.7–52.3 | 104–106 | 0.0599 | 40–45 | 2 | 634 | ±232 | 93 |
| | XVI-2 | 90 | 3 | 51.9 | 51.7–52.7 | 94–97 | 0.1101 | 45 | 3 1/6 | 630 | ±54 | 22 |
| | VI-2 | 67 | 3 | 52.5 | 52.5–52.5 | 100–106 | 0.0569 | 45 | 2½ | 609 | ±81 | 33 |
| | XII | 89 | 3 | 51.2 | 51.2–51.2 | 94–102 | 0.0935 | 45–50 | 3½ | 603 | ±13 | 5.3 |
| | X-1 | 62/55 | 1 | 52.2 | — | 101 | 0.0598 | 45 | 6½ | 553 | — | — |
| | XII | 87 | 2 | 50.1 | 50.1–50.1 | 102 | 0.0830 | 45 | 8 1/6 | 545 | ±293 | 33 |
| | IV | 7 | 1 | 54.6 | — | 128 | 0.0923 | <50 | 12 | 444 | — | — |
| Poor | XIII-2 | 81 | 3 | 48.2 | 48.1–48.6 | 99–104 | 0.0194 | 55 | 3½ | 885 | ±192 | 77 |
| | XX-4 | 75 | 2 | 41.6 | 41.4–41.8 | 104–106 | 0.0225 | 50–55 | 3½ | 883 | ±2615 | 291 |
| | XX-1 | 78 | 3 | 51.05 | 51.0–51.1 | 100–104 | 0.0275 | >55 | 4½ | 843 | ±171 | 69 |
| | XXXIII | 116 | 5 | 48.05 | 48.0–48.1 | 16 | 0.0277 | 55 | 2½ | 836 | ±52 | 42 |
| | VII-1 | 66 | 1 | 49.6 | — | 107 | n.d. | 50(g) | 2 | 819.5 | — | — |
| | XIII-2 | 95 | 3 | 43.2 | 43.2–43.2 | 96–98 | 0.0233 | 50–55 | 3½ | 816 | ±22 | 89 |
| | XIII-2 | 99 | 3 | 45.1 | 44.8–45.3 | 79 | 0.0203 | 50–55 | 2 | 812 | ±151 | 61 |
| | XXVII-3 | 72 | 3 | 43.8 | 43.6–43.9 | 104–106 | n.d. | 50–55 | 4 | 800 | ±311 | 125 |
| | XIV-3 | 97 | 2 | 47.9 | 47.9–47.9 | 94–95 | 0.0197 | 55 | 2½ | 773 | ±853 | 95 |
| Experimental | XXX-2 | 98 | 6 | 39.3 | 39.2–39.6 | 71–90 | 0.0157 | 55(g) | 2½ | 765 | ±40 | 38 |

TABLE XVI-continued
Flexure Strength (Three Point)

| Category | Filler | | Mix No. | n | Resin in Mixed Paste, Vol.% (Bar) | | | Aging, Days in Distilled Water 37±1° C. | Water Pickup, gm/ml, Mean (on Specimen | Opacity$^a$ $C_{0.70}$ ×10$^{-2}$ | Approx. Setting Time, min. 22±1° C. 50-55% Humidity (max) | Flexure Strength kg/cm$^2$ | | |
|---|---|---|---|---|---|---|---|---|---|---|---|---|---|---|
| | Filler | Type | | | Mean | Range | | | | | | Mean | Std Error of Mean at 95% | Std Deviation |
| Trans- lucency or Grainy | Filler Products | XXIX | 103 | 6 | 41.7 | 41.65-41.8 | | 66-73 | 0.0151 | 50-55 | 3 | 732 | ±79 | 76 |
| | | VII-2 | 71 | 1 | 49.9 | — | | 106 | 0.1010 | 55 | 2¾ | 725 | — | — |
| | | XXIII-2 | 84 | 1 | 42.4 | — | | 103 | n.d. | 45-24¼ | 710 | — | — | — |
| | | XXIII-1 | 79 | 1 | 42.2 | — | | 104 | n.d. | 50-55(g) | 3¾ | 690 | — | 51 |
| | | XXVII-1 | 80 | 3 | 43.25 | 43.2-43.3 | | 100-104 | 0.0299 | 50-55 | 4¼ | 679 | ±127 | 26 |
| | | XXIV | 77 | 3 | 43.2 | 43.0-43.5 | | 99-104 | 0.0262 | 50-55 | 4¼ | 666 | ±64 | — |
| | | XIX | 105 | 1 | 48.8 | 48.8-48.8 | | 66-73 | 0.0621 | 50-55(g) | 15¾ | 661 | — | 89 |
| | | XI | 85 | 3 | 53.5 | 53.5-53.5 | | 92-100 | 0.0245 | 55 | 5 | 660 | ±220 | 46 |
| | | XXIV | 76 | 3 | 39.2 | 39.0-39.0 | | 99-104 | 0.1228 | 50-55(g) | 3¾ | 641 | ±113 | 25 |
| | | XVI-1 | 86 | 3 | 46.2 | 46.2-46.2 | | 93-100 | 0.0873 | 40-45(g) | 2¾ | 639 | ±62 | 47 |
| | | XI | 88 | 3 | 52.85 | 52.8-52.9 | | 92-102 | 0.0186 | 55 | 3 | 612 | ±241 | 86 |
| | | III | 9 | 5 | 43.1 | 42.9-43.2 | | 107-134 | 0.0292 | 40-45(g) | 3 | 602 | ±106.3 | 33 |
| | | XXX-1 | 102 | 8 | 44.1 | 44.0-44.2 | | 66-74 | 0.0302 | 45(g) | 2¼ | 583 | ±27.8 | 135 |
| | | XXIII-1 | 82 | 2 | 48.55 | 48.5-48.6 | | 95-99 | 0.0317 | 50-55(g) | 3 | 558 | ±1210.5 | — |
| | | XXV-2 | 74 | 1 | 48.7 | — | | 106 | 0.0558 | 50(g) | 3 | 542 | — | 31 |
| | | IX | 63/65 | 3 | 56.5 | 56.4-56.5 | | 100-107 | 0.0367 | 50-55 | 3¾ | 507 | ±77.2 | 60 |
| | | XXV-3 | 83 | 2 | 39.6 | 39.3-39.9 | | 95-103 | | 45-50(g) | 2¼ | 479 | ±541 | — |
| | | XIX | 105 | 2 | 48.8 | 48.8-48.8 | | 66-73 | 0.0621 | 50-55(g) | 15¾ | 475 | ±416 | 167 |
| | | IX | 65/56 | 1 | 59.6 | — | | 96 | n.d. | >55 | 1¾ | 443 | — | — |
| Good Trans- lucency | Experimental Commercial and Frit Filler Blend Products (Experi- mental Filler Vol.% in the Filler Fraction in Type Column) | 13-XVII-1 (67.8%) | 110 | 5 | 50.55 | 50.5-50.6 | | 66-70 | 0.0383 | 40-45 | 5¾ | 957 | ±21 | 17 |
| | | 12-II-1 (32.0%) | 49 | 5 | 46.8 | 46.5-47.0 | | 108-140 | 0.0495 | 40-45 | 2 | 924 | ±58 | 46 |
| | | 11-II-3 (42.5%) | 46 | 5 | 46.1 | 46.0-46.2 | | 110-140 | 0.0523 | 40 | 1¾ | 870 | ±94 | 76 |
| | | 10-II-3 (75.0%) | 45 | 5 | 49.3 | 49.3-49.3 | | 108-136 | 0.0749 | 35-40 | 2 | 816 | ±211 | 170 |
| | | 1-I (50.0%) | 35 | 2 | 47.75 | 47.7-47.8 | | 132-136 | 0.0285 | 40-45 | 2 | 814 | ±159 | 18 |
| | | 14-XIX (68.2%) | 109 | 6 | 50.0 | 49.7-50.2 | | 66-72 | 0.0465 | 45-50(g) | 1¾ | 793 | ±61 | 58 |
| | | 5-I (30.5%) | 39 | 5 | 45.55 | 45.5-45.7 | | 113-135 | 0.0316 | 45 | 3 | 731 | ±72 | 58 |
| | | 4-I (40.0%) | 38 | 1 | 42.6 | — | | 143 | n.d. | n.d. | <¾ | 640 | — | — |
| | | 2-I (50.0%) | 36 | 1 | 42.6 | — | | 130 | n.d. | n.d. | <¾ | 616 | — | — |
| | | 9-IV (50.0%) | 43 | 4 | 52.1 | 52.0-52.3 | | 112-134 | 0.0749 | n.d. | ¾ | 563 | — | — |
| | | 8-IV (25.0%) | 42 | 2 | 46.8 | 46.7-46.9 | | 132-140 | 0.0446 | 40-45 | 2 | 515 | ±1.3 | 0.2 |
| | | 6-IV (50.0%) | 40 | 2 | 43.8 | — | | 134 | n.d. | n.d. | 10 | 405 | ±329 | 37 |

TABLE XVI-continued

Flexure Strength (Three Point)

| Category | Filler Type | Mix No. | n | Resin in Mixed Paste, Vol.% (Bar) Mean | Range | Aging, Days in Distilled Water 37±1° C. | Water Pickup, gm/ml, Mean (on Specimen | Opacity[a] $C_{0.70}$ x$10^{-2}$ | Approx. Setting Time, min. 22±1° C. 50-55% Humidity (max) | Flexure Strength kg/cm² Mean | Std Error of Mean at 95% | Std Deviation |
|---|---|---|---|---|---|---|---|---|---|---|---|---|
| Good Trans- lucency | f | 24 | 2 | 43.3 | 43.3-43.3 | 132-136 | n.d. | 35-40 | 1¼ | 1115 | ±1116 | 124 |
| | n | 26 | 2 | 45.45 | 45.4-45.5 | 132-140 | n.d. | 35-40 | 1¼ | 1114 | ±934 | 48 |
| | q | 50 | 4 | 48.0 | 48.0-48.0 | 112-135 | n.d. | 40 | 1¼ | 981 | ±102 | 64 |
| Experi- mental Commercial Filler Products | D | 12 | 2 | 42.2 | 42.2-42.2 | 132-136 | 0.0158 | <35 | 2 | 936 | ±81 | 10 |
| | R | 29 | 2 | 40.5 | 40.5-40.5 | 134-143 | n.d. | 40-45 | 1¼ | 934 | ±530 | 59.0 |
| | P | 34 | 2 | 50.3 | 49.9-50.8 | 134-143 | 0.0223 | n.d. | <¾ | 913 | ±23 | 3 |
| | I | 16 | 7 | 39.7 | 39.3-40.0 | 110-135 | 0.0174 | <35 | 3 | 908 | ±45 | 49 |
| | F | 2 | 2 | 39.5 | 38.8-40.2 | 132-135 | 0.0193 | 35-40 | 1½ | 848 | ±934 | 104 |
| | H | 15 | 2 | 39.4 | 39.4-39.4 | 132-143 | n.d. | 40 | 1½ | 823 | ±37 | 4 |
| Poor Trans- lucency | i | 27 | 5 | 44.35 | 44.3-44.4 | 110-135 | 0.0229 | 50-55 | 2 | 1068 | ±148 | 12 |
| | e | 23 | 3 | 38.1 | 38.0-38.15 | 126-135 | n.d. | 55 | 1½ | 1034 | ±261 | 105 |
| | j | 28 | 2 | 46.45 | 46.4-46.5 | 129-134 | 0.0211 | 50-55 | 2 | 1022 | ±202 | 134 |
| Experimental Commercial Filler Products | b | 20 | 3 | 40.1 | 39.9-40.2 | 130-135 | 0.0202 | 55 | 1½ | 940 | ±51 | 21 |
| | c | 21 | 3 | 43.5 | 43.4-43.5 | 125-135 | n.d. | 55 | 1½ | 930 | ±112 | 45 |
| | a | 19 | 2 | 38.1 | 37.7-38.5 | 128-134 | 0.0177 | >55 | 1½ | 901 | ±230 | 26 |
| | G | 13 | 6 | 41.3 | 41.2-41.4 | 110-135 | 0.0193 | 35-40(g) | 2½ | 882 | ±49 | 47 |
| | r | 51 | 2 | 52.3 | 52.25-52.3 | 137-140 | 0.0253 | 40(g) | 1½ | 838 | ±427 | 48 |
| | d | 22 | 3 | 36.2 | 36.2-36.2 | 126-135 | n.d. | 50-55 | 1½ | 829 | ±440 | 177 |
| | B | 3 | 3 | 38.6 | 38.5-38.8 | 126-135 | 0.0198 | 55 | 1 | 700 | ±504 | 203 |

[a]Grainy products denoted by (g).
[b]X-ray opacifying.

All specimen break tests were conducted with an Instron testing machine at 22°±1° C. and 50-55% humidity. Bar specimens had a flexural length of 11.943 mm as determined by the spacing between hardened steel support bars. A three point load was applied with a crosshead speed of 0.05 inches per minute. The support bars and the load edge were covered with a double-sticky Scotch tape to inhibit slippage.

(i) Water pickup.—Water pickup was determined on selected bars and plates used to determine translucency. Two methods were used to evaluate the water absorption. In both methods the amount of water absorbed in grams was determined as the difference between the initial and final weights of the specimens.

One method involves the determination of specimen volume and stating the number of grams of water absorbed per milliliter of specimen (Table XVII). Bar volumes were determined by direct calculation from measured specimen dimensions. Volumes of the translucency plates used for water pickup determinations were obtained hydrostatically.

TABLE XVII

| | | | Water Pickup by Volume of Specimen | | | | |
|---|---|---|---|---|---|---|---|
| Filler | Mix. No. | Resin in Mixed Paste, Vol. % (Mean of All Bars) | Mean Bar gm/ml $\times 10^{-2}$ (Except Where Foot-noted) | Std Error of Mean at 95%, gm/ml $\times 10^{-2}$ | Std Deviation gm/ml $\times 10^{-2}$ | Aging, Days in Distilled Water 37 ± 1° C. | |
| | | | | | | n, Bars Bars | Translucency Specimen No. |
| Adaptic | | 39.0 | 1.194 | ±0.322 | 0.342 | 7 60-117 | — |
| Cosmic | | n.d. | 1.299 | ±0.079 | 0.076 | 6 16-14 | — |
| Prestige | | n.d. | 1.372 | ±0.047 | 0.045 | 6 15-16 | — |
| XXIX | 103 | 41.7 | 1.505 | ±0.095 | 0.090 | 6 66-74 | 75 |
| XXX-2 | 98 | 39.3 | 1.572 | ±0.110 | 0.105 | 6 71-90 | — |
| D | 12 | 42.2 | 1.576 | — | — | 1 136 | — |
| I | 16 | 39.7 | 1.736 | ±0.218 | 0.137 | 4 110-135 | — |
| a | 19 | 38.1 | 1.770 | — | — | 1 120 | — |
| III | 9 | 43.1 | 1.058 | ±0.750 | 0.302 | 3 107-129 | — |
| G | 13 | 41.3 | 1.925 | ±0.929 | 0.103 | 2 126-115 | — |
| F | 2 | 39.5 | 1.928 | — | — | 1 132 | — |
| XIII-2 | 81 | 48.2 | 1.930 | — | — | 1 104 | — |
| XIV-3 | 97 | 47.9 | 1.966 | — | — | 1 95 | — |
| b | 3 | 38.6 | 1.975 | — | — | 1 130 | — |
| b | 20 | 40.1 | 2.018 | ±0.212 | 0.0054 | 3 126-135 | 115 |
| XVII-2 | 99 | 45.1 | 2.027 | ±0.1925 | 0.0775 | 3 79-79 | — |
| j | 28 | 46.45 | 2.105 | — | — | 1 134 | — |
| v | 6 | 46.45 | 2.196 | ±1.566 | 0.174 | 2 110-134 | — |
| p | 34 | 50.3 | 2.230 | — | — | 1 134 | — |
| XXV-4 | 75 | 41.6 | 2.247 | ±0.076 | 0.0085 | 2 104-106 | — |
| I | 27 | 44.35 | 2.294 | — | — | 1 113 | — |
| XVIII | 106 | 47.7 | 2.304 | ±0.186 | 0.2225 | 8 66-73 | — |
| XIII-2 | 95 | 43.2 | 2.330 | — | — | 1 88 | 89 |
| XXVII-2 | 84 | 42.4 | 2.380$^a$ | — | — | 0 — | 96 |
| XXVIII | 107 | 44.85 | 2.392 | ±0.103 | 0.098 | 6 59-87 | 72 |
| XXIV | 76 | 39.2 | 2.446 | — | — | 1 103 | — |
| XIII-1 | 94 | 44.9 | 2.489 | ±0.966 | 0.1075 | 2 94-98 | 90 |
| r | 51 | 52.3 | 2.530 | — | — | 1 140 | — |
| Glass bead std A | 111 | 46.6 | 2.597 | ±0.065 | 0.070 | 7 63-70 | 69 |
| XXIV | 77 | 43.2 | 2.619 | — | — | 1 100 | — |
| XXVII-3 | 72 | 43.8 | 2.460$^a$ | — | — | 0 — | 100 |
| XX-1 | 78 | 51.05 | 2.751 | ±0.305 | 0.034 | 2 104-104 | — |
| XXXII | 116 | 48.05 | 2.767 | ±0.0765 | 0.073 | 6 16-16 | 27 |
| 1 (I = 50.0%) | 35 | 47.75 | 2.854 | — | — | 1 132 | — |
| XXX-1 | 102 | 44.1 | 2.917 | ±0.219 | 0.236 | 7 66-74 | 76 |
| XXVII-1 | 80 | 43.25 | 2.980$^a$ | — | — | 0 — | v |
| XXXIII-1 | 82 | 48.55 | 3.015$^a$ | — | — | 1 99 | — |
| Glass bead std A | 8 | 46.8 | 3.101 | ±0.4835 | 0.304 | 4 112-140 | 114 |
| I | 5 | 47.6 | 3.109 | ±0.475 | 0.053 | 2 107-108 | — |
| XXXIII | 115 | 62.4 | 3.158 | ±0.284 | 0.271 | 6 19-27 | 27 |
| 5 (I = 30.5%) | 39 | 45.55 | 3.160 | ±0.313 | 0.197 | 4 113-135 | — |
| XXV-2 | 74 | 48.7 | 3.170 | — | — | 1 106 | — |
| XXII | 100 | 50.0 | 3.280 | ±0.226 | 0.245 | 7 69-79 | 76 |
| XXV-3 | 83 | 39.6 | 3.669 | ±2.274 | 0.253 | 2 95-103 | — |
| XXVI | 104 | 44.65 | 3.700 | ±0.266 | 0.253 | 6 66-74 | — |
| 13 (XVII-1 = 67.8%) | 110 | 50.55 | 3.827 | ±0.116 | 0.112 | 6 66-70 | 69 |
| IX | 65, 56 | 59.6 | 4.255$^a$ | — | — | 0 — | 113 |
| 8 (IV = 25.0%) | 42 | 46.8 | 4.459 | — | — | 1 132 | — |
| 14 (XIX = | | | | | | | |

TABLE XVII-continued

Water Pickup by Volume of Specimen

| Filler | Mix. No. | Resin in Mixed Paste, Vol. % (Mean of All Bars) | Mean Bar gm/ml × 10⁻² (Except Where Footnoted) gm/ml × 10⁻² | Std Error of Mean at 95%, gm/ml × 10⁻² | Std Deviation gm/ml × 10⁻² | n, Bars | Aging, Days in Distilled Water 37 ± 1° C. Bars | Translucency Specimen No. |
|---|---|---|---|---|---|---|---|---|
| 68.2%) | 109 | 50.0 | 4.646 | ±0.074 | 0.070 | 6 | 66–72 | 69 |
| XVII-1 | 108 | 54.2 | 4.851 | ±0.706 | 0.284 | 3 | 66–72 | — |
| XIV-2 | 96 | 42.2 | 4.900 | ±0.197 | 0.022 | 2 | 88–98 | 89 |
| 12 (II-1 = 32.0%) | 49 | 46.8 | 4.951 | — | — | 1 | 140 | — |
| 11 (II-3 = 42.5%) | 46 | 46.1 | 5.229 | — | — | 1 | 140 | — |
| IX | 63, 65 | 56.5 | 5.580 | — | — | 1 | 100 | — |
| XXXI | 101 | 39.7 | 5.654 | ±0.189 | 0.180 | 6 | 68–77 | 77 |
| VI-2 | 67 | 52.5 | 5.688 | — | — | 1 | 106 | 105 |
| X-1 | 70 | 50.1 | 5.703 | — | — | 1 | 103 | 105 |
| 9 (IV = 50.0%) | 43 | 52.1 | 5.767ᵃ | — | — | 0 | — | 113 |
| VI-1 | 69 | 51.9 | 5.987 | ±0.667 | 0.074 | 2 | 104–106 | — |
| X-2 | 68 | 52.3 | 6.072 | — | — | 1 | 107 | — |
| XIX | 105 | 48.8 | 6.214 | ±1.680 | 0.676 | 3 | 66–73 | 72 |
| II-2 | 10 | 56.7 | 6.291 | ±3.500 | 0.390 | 2 | 107–134 | 113 |
| IX | 44 | 47.8 | 6.308 | ±2.896 | 0.322 | 2 | 112–135 | — |
| VII-1 | 60 | 49.6 | 6.780ᵃ | — | — | 0 | — | 103 |
| XV-1 | 92 | 45.5 | 6.912 | — | — | 1 | 96 | — |
| 10 (II-3 = 75.0%) | 45 | 49.3 | 7.487 | ±0.011 | 0.0015 | 2 | 112–126 | — |
| XII | 87 | 56.1 | 8.301 | — | — | 1 | 102 | — |
| II-3 | 11 | 47.0 | 8.401 | ±0.036 | 0.336 | 1 | 113–112 | — |
| XI | 85 | 51.5 | 8.621 | — | — | 1 | 92 | — |
| XI | 88 | 52.85 | 8.732 | — | — | 1 | 92 | — |
| IV | 7 | 54.6 | 9.224 | — | — | 1 | 128 | — |
| XII | 89 | 61.2 | 9.151 | ±3.703 | 0.412 | 2 | 91–108 | 11 |
| XVI-2 | 96 | 51.9 | 11.011 | ±0.966 | 0.1075 | 2 | 91–27 | — |
| III | 14 | 44.2 | 11.722 | — | — | 1 | 134 | 111 |
| XVI-1 | 86 | 46.2 | 17.281 | ±9.871 | 0.650 | 3 | 33–79 | 11 |

ᵃTranslucency plate determinations

The other method involves calculating the volume of solids in the specimen. Water pickup is then expressed as the grams of water absorbed per volume of mixed paste in the specimen, i.e. the sum of the volumes of filler and resin. This expression of absorbed water ignores the effect of voids (Table XVIII).

TABLE

Water Pickup by Volume of Solid Paste

| Filler | Mix No. | Resin in Mixed Paste, Vol % (Mean of All Bars) | Mean Bar gm/ml m 10⁻³ Except Where Footnoted | Std Error of Mean at 95% gm/ml m 10⁻² | Std Deviation gm/ml m 10⁻² | n, Bars | Difference in Mean Water Pickup of Bars from Translucency Specimens | Aging, Days in Distilled Water 37 ± 1° C. Bars | Translucency Specimen No. |
|---|---|---|---|---|---|---|---|---|---|
| XXIX | 103 | 41.7 | 1.569 | ±0.1203 | 0.1146 | 6 | −0.370 | 66–74 | 75 |
| XXX-2 | 99 | 39.3 | 1.438 | ±0.123 | 0.1175 | 6 | −0.129 | 71–90 | 78 |
| D | 12 | 42.2 | 1.638 | — | — | 1 | n.d. | 136 | — |
| d | 22 | 36.2 | 1.743 | — | — | 0 | n.d. | — | — |
| I | 16 | 39.7 | 1.801 | ±0.257 | 0.162 | 4 | −0.080 | 110–135 | 114 |
| a | 19 | 38.1 | 1.842 | — | — | 1 | −0.160 | 120 | 115 |
| III | 9 | 43.1 | 1.932 | ±0.773 | 0.111 | 3 | −0.063 | 107–129 | 113 |
| XIII-2 | 81 | 48.2 | 1.943 | — | — | 1 | −0.368 | 104 | 98 |
| N | 15 | 39.4 | 1.973ᵃ | — | — | 0 | n.d. | — | 118 |
| F | 2 | 39.5 | 2.022 | — | — | 1 | +0.190 | 132 | 118 |
| G | 13 | 41.3 | 2.033 | ±1.194 | 0.133 | 2 | +0.031 | 126–135 | 118 |
| XIV-3 | 97 | 47.9 | 2.034 | — | — | 1 | +0.294 | 95 | 89 |
| 3 | 9 | 38.6 | 2.043 | — | — | 1 | +0.253 | 130 | 115 |
| 0 | 23 | 38.1 | 2.136ᵃ | — | — | 0 | n.d. | — | 115 |
| b | 20 | 40.1 | 2.139 | ±0.251 | 0.101 | 3 | +0.345 | 126–135 | 115 |
| XVII-2 | 99 | 45.1 | 2.183 | ±0.259 | 0.104 | 3 | −0.121 | 79–79 | 76 |
| v | 4 | 46.45 | 2.223 | ±1.455 | 0.162 | 2 | +0.059 | 110–134 | 115 |
| ν | 34 | 50.3 | 2.281 | — | — | 1 | n.d. | 134 | — |

TABLE-continued

Water Pickup by Volume of Solid Paste

| Filler | Mix No. | Resin in Mixed Paste, Vol % (Mean of All Bars) | Mean Bar gm/ml m $10^{-3}$ Except Where Footnoted | Std Error of Mean at 95% gm/ml m $10^{-2}$ | Std Deviation gm/ml m $10^{-2}$ | n, Bars | Difference in Mean Water Pickup of Bars from Translucency Specimens | Aging, Days in Distilled Water 37 ± 1° C. Bars | Translucency Specimen No. |
|---|---|---|---|---|---|---|---|---|---|
| 3 | 28 | 46.45 | 2.310 | — | — | 1 | ±0.345 | 134 | 118 |
| c | 21 | 43.5 | 2.332$^a$ | — | — | 0 | n.d. | — | 115 |
| XVIII | 106 | 47.7 | 2.410 | ±0.192 | 0.230 | 8 | ±0.399 | 66–73 | 72 |
| q | 50 | 48.0 | 2.464 | — | — | 1 | +0.564 | 126 | 115 |
| XXV-4 | 75 | 41.6 | 2.478 | ±0.489 | 0.054 | 2 | −0.312 | 104–106 | 99 |
| XXVIII | 107 | 44.85 | 2.497 | ±0.125 | 0.119 | 6 | +0.058 | 58–87 | 72 |
| i | 27 | 44.35 | 2.504 | — | — | 1 | +0.574 | 113 | 118 |
| XIII-1 | 94 | 44.9 | 2.505 | ±0.419 | 0.047 | 2 | −0.132 | 94–98 | 90 |
| XXIII-1 | 79 | 42.2 | 2.526$^a$ | — | — | 0 | n.d. | — | 98 |
| XIII-2 | 95 | 43.2 | 2.533 | — | — | 1 | −0.253 | 88 | 89 |
| XXVII-2 | 84 | 42.4 | 2.620$^a$ | — | — | 0 | n.d. | — | 96 |
| r | 51 | 52.3 | 2.635 | — | — | 1 | n.d. | 140 | — |
| XXIV | 76 | 39.2 | 2.687 | — | — | 1 | +0.557 | 103 | 99 |
| Glass bead Std.A | 111 | 46.6 | 2.699 | ±0.049 | 0.053 | 7 | −0.140 | 63–70 | 69 |
| XXIV | 77 | 43.2 | 2.835 | — | — | 1 | +0.233 | 100 | 98 |
| XX-1 | 78 | 51.05 | 2.900 | ±0.470 | 0.052 | 2 | −0.243 | 104–104 | 98 |
| XXVII-3 | 72 | 43.8 | 2.907$^a$ | — | — | 0 | n.d. | — | 100 |
| I (I=50.0%) | 35 | 47.75 | 2.975 | — | — | 1 | n.d. | 132 | — |
| XXXII | 116 | 48.05 | 2.993 | ±0.0852 | 0.081 | 6 | −0.742 | 16–16 | 27 |
| XXXIII-1 | 82 | 48.55 | 3.092 | — | — | 1 | −0.741 | 99 | 96 |
| −1 | 102 | 42.1 | 1.156 | ±0.259 | 0.280 | 7 | −0.727 | 66–74 | 76 |
| Glass bead Std.A | 8 | 46.5 | 3.256 | ±0.574 | 0.361 | 4 | −0.348 | 112—140 | 114 |
| 5 (I=30.5%) | 39 | 45.55 | 3.269 | ±0.376 | 0.236 | 4 | +0.279 | 113–135 | 115 |
| I | 5 | 47.6 | 3.287 | ±0.2795 | 0.0311 | 2 | +0.382 | 107–108 | 114 |
| XXVII-1 | 80 | 43.25 | 3.359$^a$ | — | — | 0 | n.d. | — | 98 |
| XXII | 100 | 50.0 | 3.398 | ±0.240 | 0.259 | 7 | −0.243 | 69–79 | 76 |
| XXXIII | 115 | 62.4 | 3.405 | ±0.316 | 0.301 | 6 | +0.247 | 19–27 | 27 |
| XXV-2 | 74 | 48.7 | 3.492 | — | — | 1 | −0.237 | 106 | 99 |
| XXVI | 104 | 44.65 | 3.861 | ±0.289 | 0.275 | 6 | −0.385 | 66–74 | 75 |
| 13 (XVII-1 =67.8%) | 110 | 50.55 | 4.177 | ±0.121 | 0.116 | 6 | −0.074 | 66–70 | 69 |
| XIV-4 | 93 | 41.7 | 4.356$^a$ | — | — | 0 | n.d. | — | 91 |
| XXV-3 | 83 | 39.6 | 4.384 | ±2.827 | 0.315 | 2 | −1.265 | 95–103 | 96 |
| IX | 65/56 | 59.6 | 4.632$^a$ | — | — | 0 | n.d. | — | 113 |
| 8(IV=25%) | 42 | 46.8 | 4.762 | — | — | 1 | n.d. | 132 | 118 |
| 14 (XIX = 68.2%) | 109 | 50.0 | 4.949 | ±0.082 | 0.078 | 6 | −0.228 | 66–72 | 69 |
| 12(II-1 =32.0%) | 49 | 46.8 | 5.187 | — | — | 1 | +0.421 | 140 | — |
| XIV-2 | 96 | 42.2 | 5.293 | ±0.108 | 0.012 | 2 | +0.214 | 88–98 | 89 |
| XVII-1 | 108 | 54.2 | 5.341 | ±0.549 | 0.221 | 3 | −0.749 | 66–72 | 72 |
| 11(II-3 +42.5%) | 46 | 46.1 | 5.666 | — | — | 1 | −0.161 | 140 | 115 |
| XXXI | 101 | 39.7 | 5.733 | ±0.235 | 0.224 | 6 | −1.115 | 68–77 | 76 |
| X-1 | 70 | 50.1 | 4.030 | — | — | 1 | −0.326 | 103 | 105 |
| IX | 63/65 | 54.5 | 6.087 | — | — | 1 | +0.529 | 100 | 105 |
| II-2 | 10 | 56.7 | 6.121 | +1.710 | 0.413 | 2 | −0.005 | 107–134 | 113 |
| X - 1 | 62/55 | 52.2 | 6.214$^a$ | — | — | 0 | n.d. | — | 114 |
| 9(IV = 50.0%) | 43 | 52.1 | 6.265$^a$ | — | — | 0 | n.d. | — | 113 |
| X-2 | 60 | 52.3 | 6.549 | — | — | 1 | −0.076 | 107 | 105 |
| VI-2 | 47 | 52.5 | 6.606 | — | — | 1 | −0.329 | 106 | 105 |
| IX | 44 | 47.8 | 6.639 | ±3.291 | 0.366 | 2 | +0.317 | 112–115 | 113 |
| VI-1 | 69 | 51.9 | 6.682 | ±1.442 | 0.141 | 2 | −0.998 | 104–106 | 105 |
| XIX | 105 | 48.8 | 7.060 | ±0.373 | 0.150 | 3 | +0.087 | 66–73 | 72 |
| VII-1 | 66 | 49.6 | 7.719$^a$ | — | — | 0 | n.d. | — | 103 |
| XV-1 | 92 | 45.5 | 7.729 | — | — | 1 | −0.025 | 96 | 91 |
| 10 (II-3= | 45 | 49.3 | 0.359 | ±1.404 | 0.156 | 2 | +0.071 | 112–126 | 113 |

TABLE-continued

| | | | | | | | Difference in Mean Water Pickup of Bars from | Aging, Days in Distilled Water 37 ± 1° C. | |
|---|---|---|---|---|---|---|---|---|---|
| | | Resin in Mixed Paste, Vol % | Mean Bar gm/ml m 10⁻³ Except Where Foot- | Std Error of Mean at 95% gm/ml | Std Devia- tion gm/ml | | Trans- lucency Speci- | | Trans- lucency Speci- |
| Filler | Mix No. | (Mean of All Bars) | noted) | m 10⁻² | m 10⁻² | n, Bars | mens | Bars | men No. |
| 75.0%) | | | | | | | | | |
| XII | 87 | 50.1 | 9.063 | — | — | 1 | −2.127 | 102 | 93 |
| ZI | 80 | 52.85 | 9.304 | — | — | 1 | −0.444 | 92 | 93 |
| XI | 85 | 83.5 | 9.327 | — | — | 1 | −0.997 | 92 | 93 |
| II-3 | 11 | 47.0 | 9.707 | ±1.344 | 0.541 | 3 | n.d. | 113–132 | — |
| XII | 89 | 51.3 | 9.071 | ±0.356 | 0.040 | 2 | −1.112 | 96–102 | 93 |
| VII-2 | 71 | 49.9 | 10.530$^a$ | — | — | 0 | n.d. | — | 105 |
| IV | 7 | 54.4 | 10.560 | — | — | 1 | n.d. | 128 | — |
| XVI-2 | 90 | 51.9 | 11.949 | ±1.200 | 0.144 | 2 | −0.025 | 94–97 | 91 |
| III | 14 | 44.2 | 12.567 | — | — | 1 | +0.816 | 134 | 113 |
| XVI-1 | 96 | 46.2 | 13.996 | ±6.753 | 0.752 | 2 | −0.016 | 93–100 | 93 |

$^a$Translucency plate determinations

It is to be noted that in determining water pickup dessicator techniques are unnecessary because the water absorption from the air at 22°±1° at 50-55% relative humidity was experimentally insignificant. All specimen weight determinations were determined within one hour after removal from the 37°±1° C. oven and after having attained room temperature (22°±1° C.). It appeared that water exchange in the specimens accommodating to lower temperature conditions could be ignored.

(j) Finishability.—Trapezohedral cavities were drilled to opposite sides of molars to a depth of approximately one mm. The cavity was cleaned so that there were no rough edges on the enamel surface. A mold was made utilizing a cervical matrix form that conformed to the contours of the tooth. A wax blob was used to hold the matrix form in place after placement of the mixed paste in the cavity.

Most mixed pastes were injected by syringes into the tooth cavities. One was spatula filled and tamped in; another was a combination of syringe filling followed by spatula filling and tamping (Table XIX). In all cases the mold was placed over the filled cavity within 1½ minutes after the start of the mixing and held tightly in place to prevent air reaching the filling. The mold was held manually in place for 5-10 minutes and then carefully removed.

TABLE XIX

Finishability (Arranged in Order with the Best Finish at Top)

| Filler | Mix No. | Resin in Mixed Paste Vol. % (Translucency Specimens) | Preparation Conditions | | | Oblique Light Examination[a] | | SEM Examination | Opacity $C_{0.70}$ $\times 10^{-2}$ | Sieve Size | | Flexure Modulus kg/cm² | |
|---|---|---|---|---|---|---|---|---|---|---|---|---|---|
| | | | Mix Time, Sec. | Mold Time, Min. | Application | ×38 | ×500 | | | +200 Vol % | −400 Vol % | Mean | Std Error of Mean at 95% |
| XI | 88 | 52.8 | 30 | 10.3 | Syringe filled | Same-to-better than tooth, large bubbles | Same as tooth, many bubbles | n.d. | 55 | — | 67.4 | 611.9 | ±240.8 |
| X-2 | 68 | 52.2 | 32 | 6.2 | Syringe filled | Same-to-better than tooth, many bubbles | Slightly rougher than tooth | n.d. | 40-45 | — | 86.3 | 805.7 | ±129.4 |
| XVI-1 | 86 | 46.2 | 30 | 10 | Syringe filled | Same as tooth, large bubbles | Slightly rougher than tooth | no pitting or plucking of filler | 40-45 | 16.5 | 47.9 | 638.6 | ±2.0 |
| X-1 | 70 | 50.0 | 32 | 9.5 | Syringe filled | Same as tooth | Slightly rougher than tooth | n.d. | 40-45 | — | 80.2 | 663.6 | ±179.3 |
| XX-1 | 78 | 51.1 | 32 | 10 | Syringe filled | Same as tooth | Same as tooth | n.d. | >55 | — | 94.2 | 843.1 | ±170.9 |
| XII | 89 | 51.2 | 30 | 10 | Syringe filled | Same as tooth, large bubbles | Slightly rougher than tooth | n.d. | 45-50 | — | 47.4 | 602.6 | ±13.1 |
| XIV-2 | 96 | 42.2 | 31 | 10 | Syringe and spatula filled | Slightly rougher than tooth | Slightly rougher than tooth | No pitting or plucking of filler | 45-50 | — | 94.8 | 845.3 | ±106.8 |
| II-2 | 10 | 56.3 | 30 | 6.8 | Syringe filled | Slightly rougher than tooth | Same as tooth | n.d. | 45 | — | 100.0 | 773.5 | ±97.5 |
| XXIV | 76 | 39.0 | 30 | 10 | Spatula filled | Rougher than tooth, many bubbles. Same as Adaptic | Slightly rougher than tooth, slightly smoother than Adaptic | n.d. | 50-55 | n.d. | n.d. | 640.7 | ±113.3 |
| Adaptic | — | 39.2[b] | 30 | 10 | Syringe filled | Rougher than tooth | Rougher than tooth, worst finish obtained | Heavy pitting of filler | n.d. | n.d. | n.d. | 906.5 | ±65.7 |
| Prestige | — | n.d. | 30 | 10 | Syringe filled | n.d. | n.d. | Glass spheres plucked out | n.d. | n.d. | n.d. | 721.3 | ±59.3 |

[a]All better than Adaptic.
[b]Ref. TABLE XVI.

Directly after the mold was removed, the cavity was finished at room temperature (22°±1° C.). Using a slow speed drill with contra-angle head and a Shofu composite point, the filler was ground down to the level and contour of the tooth. Then, using a straight slow speed drill with a coarse and then fine zirconium silicate disc, the restoration was polished smooth. All the polishing and grinding surfaces were lubricated with M Q Lubricant for Silicate Restorations from S. S. White Co., Philadelphia, Pennsylvania. After both cavities were finished in the individual teeth, the teeth were cleaned with mild soap and water and refrigerated in distilled water until the finish could be observed.

An Ultrapak optical microscope obtained from Leitz Optical Co., Rockleigh, N.J., was used to assess the roughness and marginal adaptation of the prepared fillings. The specimens were mounted so that the surfaces viewed were parallel to the optic axis of the microscope. Incident light angles were maintained at a constant angle through all comparative viewings. A 10X eyepiece and 3.8 and 50X objectives were used.

In addition observations were made under the stereomicroscope and by the dentist and appeared not to contradict the Ultrapak assessment. Two of the novel filler product fillings and those of "Adaptic" and "Prestige" were subjected to SEM observation after plating with gold subsequent to degasing at 60° C. for one hour in an aspirator vacuum.

(k) X-ray opacity.—Incisal teeth were used for test specimens. Two U-shaped cavities on opposing lateral sides of the incisals were cut and filled with composite resin. The fillings were roughly finished. The contrast between dentin and enamel contacts with the experimental fillings was noted.

Filled teeth were placed in the center of a Kodak dental x-ray film. A General Electric dental x-ray machine with tungsten radiation was used to expose the film. The cone of the x-ray machine was positioned perpendicular to the film with the bottom of the cone 2.5 cm from the bottom of the film. Settings on the x-ray machine were 10 MA and 90 KVP. Exposure time was four sixteenths of a second.

TEST RESULTS (a) Filler characterization.—Prepared experimental frit filler composition in mass percent varies in $ZrO_2$, about 19–35%; $Al_2O_3$, about 13–60%; $SiO_2$, about 27–56%; and has a total of less than about 0.2% of $B_2O_3$, $P_2O_5$, $Li_2O$, $Na_2O$, and $NaF$. One frit contains about 10–11% tin (Table III). Zirconium and tin are x-raying opacifying constituents. Frits containing $HfO_2$ as an x-ray opacifying constituent have been prepared by the gel route from hafnium oxychloride hydrates. It is believed these will prove fully equivalent to the zirconium containing frits, however, they have not been evaluated.

Measured aggregate frit densities vary from about 2.37 to about 3.15 gm/cc. Median refractive indices of the frit vary from about 1.51 to about 1.64. There appears to be an approximate linear relationship between median refractive index and measured frit density.

Crystallinity as determined with optical microscopy is usually less than 5 vol. %, but does have values as high as 25 vol. %. See FIG. 1. Opalescent regions which primarily developed from inhomogeneities in the gels are usually not extended on a microscale. However, some frits have opalescent regions which appear microscopically to occupy half the volume of some frits. See Table V.

Figure 2:
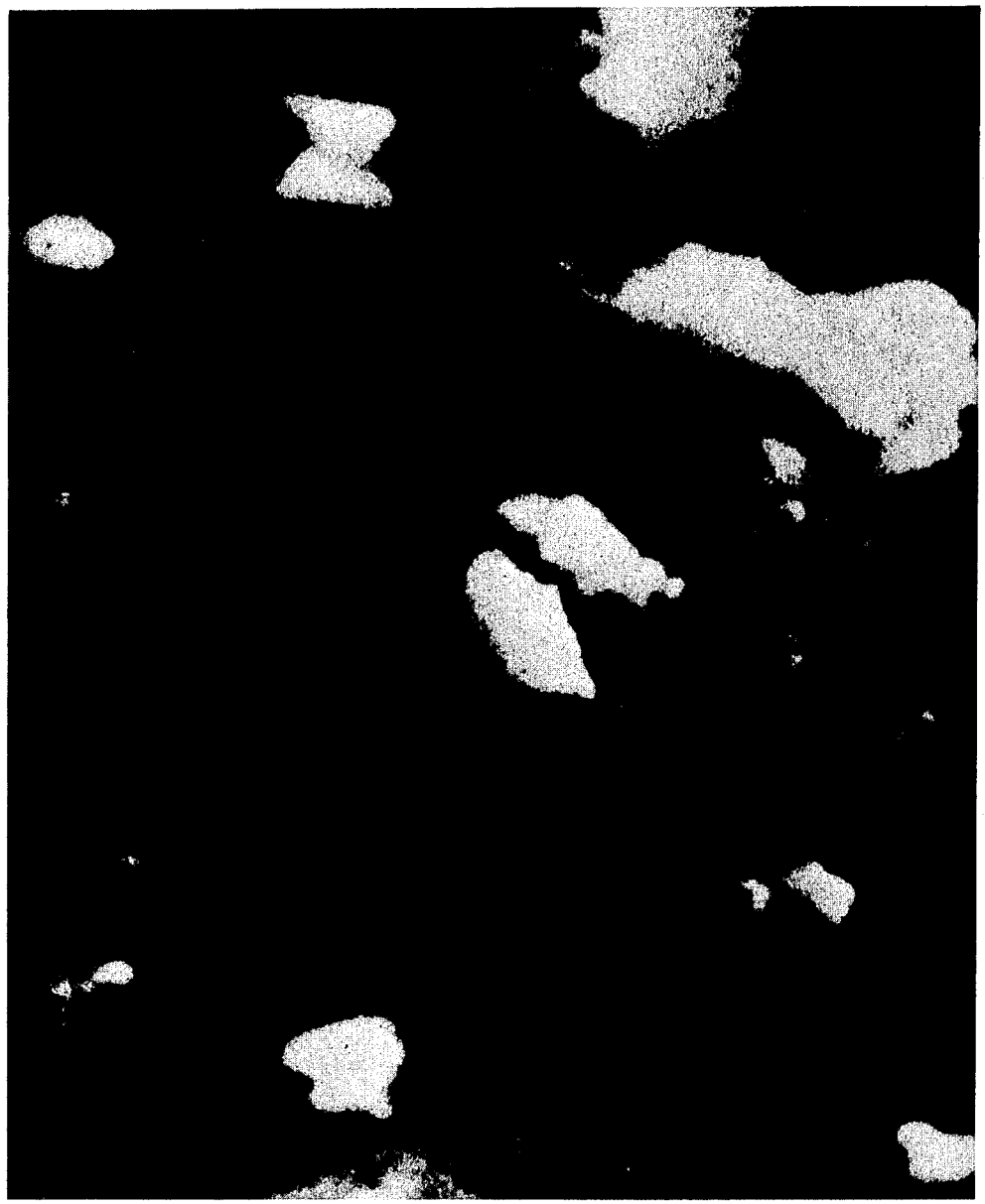
FIG. 2 shows a microscopic examination of filler frit, mix XXXII exhibiting bowl-like depressions and slightly elevated tubercle-like projections.
Figure 3:
FIG. 3 shows a microscopic examination of filler frit, mix XXXII exhibiting fine granular topographic structure due to surface expression of internal microporosity.

High magnification photographs of the surfaces of milled frit grain reveal a rough topography. Shallow bowl-shaped depressions and slightly elevated tubercles occur over particle surfaces. See FIG. 2. Particle surface topography reflects the microporosity and immiscibility structure characteristic of the experimental frits. Ultimate particle surface structure appears finely granular and is caused by the microporous structure of the frit. See FIG. 3. Surface textual features do not appear to interconnect in depth with internal microporosity.

(b) Setting contraction.—The contractions in volume obtained upon setting in distilled water at 22°±1° C. vary in the different novel filler products from 2.40 to 3.28 vol. % (Table X). At temperatures elevated to between 35° and 40° C., setting contraction ranges from 2.78 to 3.44 vol. %. Both "Adaptic" and "Prestige" commercial products show increased setting contraction at elevated-over-room temperatures, 1.80 vs. 2.40 vol. % for "Adaptic", and 2.56 vs. 3.22 vol. % for "Prestige".

"Adaptic" has the lowest measured setting contraction values both at elevated and room temperatures. It also has a higher filler content in the mixed paste, 61 vol. %, than any of our novel filler products. The highest filler content in the novel filler products tested is about 58 vol. %, although higher filler levels are possible. Both the mixed commercial glass bead filler containing product and "Prestige" appear to have setting contractions within the range of the novel filler products.

(c) Translucency.—Most of the products which have good translucency have median refractive indices which are in the middle region of the refractive index range of the novel filler products, i.e. 1.510–1.640. Factors other than median refractive index determine translucency of the prepared products. Opacity ($C_{0.70}$) may be reduced at least 0.025 by water pickup after specimen preparation.

In products made from the novel filler which have 5 vol. % or less or microcrystals, no extended opalescent or cryptocrystalline regions, and no plus-200-mesh particles, behavior is highly controlled by the refractive index. At about 48 vol. % resin in the mixed paste, opacity appears to increase linearly with increase in refractive index.

At lower resin contents, i.e. greater amounts of filler, the relationship may be more complicated. The greater the range in filler refractive index about that of the resin, the greater the opacity. If present in large amounts, microcrystals and cryptocrystalline opalescent regions greatly increase opacity. Within limits, increase in particle size promotes translucency. It is noteworthy that no novel filler with median refractive indices greater than 1.590 yielded opacities less than 0.50.

(d) Setting time.—Room temperature setting times vary over wide ranges. Products prepared utilizing the novel fillers range in setting time from less than about ⅔ min. to about 15¾ min. All products with setting times exceeding 8 min. are in the lowest strength category, less than 660 kg/cm² and distinctly weaker than "Prestige" (Table XVI).

Analysis of the data appeared to show no distinct relationship between water pickup and setting time. Within limits shorter setting times appear to be beneficial to strength. Indication of this may be found in the comparison of two products containing Corning glass bead filler 1720 and having 46–47 vol. % resin in the mixed paste (Table XVI). This glass bead product which set within 1½ min. has a mean flexure strength of 927±41 kg/cm², one which set in 3 min., a strength of 859±61 kg/cm².

Further confirmation of this setting time influence on strength is found in plots of mean flexure strength vs. vol. % resin in the mixed paste. Products setting in 4 min. or more which contain novel filler with no plus-200-mesh particles and having good translucencies have mean flexure strengths less than 760 kg/cm². However, ⅔ths of the products with setting times less than 4 min. are stronger than this.

(e) Thermal expansion.—Two products utilizing experimental filler and having 42.2 and 50.5 vol. % resin in the mixed paste have thermal expansions between 10° and 65° C., equal to or lower than "Adaptic". The 42.2 vol. % resin product, which has flexure strengths near that of "Adaptic" in thermal expansion; $27.2 \times 10^{-6}/°C$. for experimental product vs. $32.0 \times 10^{-6}/°C$. for "Adaptic" (Table XII).

(f) Microhardness.—Microhardness of the novel filler products with good translucencies (0.50 or less in opacity) and no plus-200-mesh particles appear to be linearly dependent upon the filler content of the mixed paste (Table XIII). At a higher filler or lower resin % vol. in the mixed paste, it would appear that excess of particles in the plus-200-mesh fraction reduces microhardness. This is not evident in the higher resin contents. The microhardness of "Adaptic" was found to plot on the extrapolated best-fitting line for experimental filler products having good translucency and no plus-200-mesh particles.

(g) Modulus of elasticity.—A linear relationship between resin vol. % in our novel filler product containing mixed paste and elastic modulus exists. This relationship is particularly apparent in the paste products prepared from our novel filler containing no plus-200-mesh particles. "Adaptic" lies in elastic modulus somewhat above a linear extrapolation of a best-fitting line for this relationship.

Specimens which contain plus-200-mesh filler particles tend to be lower in elastic modulus than those specimens containing no plus-200-mesh particles. This is particularly evident in those specimens having lower resin vol. % in the mixed pastes, e.g., mixes 76 and 77. However, this is not so evident in higher vol. % resin pastes, e.g. mixes (65,56) and (63,65) with 59.6 and 56.5 vol. % resin, respectively (Table XVI).

(h) Tensile strength.—Mean diametrical tensile strength for one novel product (mix #107) containing 44.8 vol. % resin in the mixed paste (Table XV) is 332±23 kg/cm². This value is only slightly less than the 362±64 kg/cm² for the higher filler content "Adaptic" (39 vol. % resin). Another product mix #104 with a slightly higher water pickup in the specimens has a lower tensile strength, 312±20 kg/cm², than product mix #107.

(i) Flexure strength.—Bar modulus of rupture or fluxure strength of specimens prepared at room temperature is very dependent upon particle size. Plus-200-mesh particles have a pronounced weakening effect. This weakening effect is apparently linearly dependent upon the vol. % of plus-200-mesh material in the novel filler products.

As previously mentioned, prolonged setting times appear to be deleterious to strength. See FIG. 10. It is to be noted that the minus-325-mesh bead filled products, mix #8 and #111, have slightly different strengths, 927±41 kg/cm² and 859±61 kg/cm², respectively. There is essentially the same vol. % resin in both mixed pastes (Table XVI). It may be that the shorter setting time of mix #8, 1½ min., may be responsible for a greater flexure strength over that of the 3 min. setting and weaker mix #111.

Addition of fused silica fiber to pastes containing fused silica chips was found to increase greatly flexure strength. Small amounts of fused silica fiber when blended with the novel frits is capable of greatly increasing strength. For example, the filler blend #13 with 6.1 vol. % fused silica fiber and 26.1 vol. % minus-325-mesh glass beads and 67.8 vol. % of an x-ray opacifying frit (XVII-I) yields a paste which has a flexure strength of 957±21 kg/cm² (Tables VIII and XVI).

The high strength of mix #110 was attained with a resin content of 50.55 vol. %. "Adaptic" with a resin content of 39.0 vol. % has a lower flexure strength of 907±66 kg/cm² (Table XVI). Glass bead, mixes #8 and #111, and novel frit paste, mix #108, all have lower flexure strengths than the silica fiber blend.

Examination of the flexure strength data for products containing no plus-200-mesh particles and having a good translucency reveals that strength tends to increase as the filler content increases. Those novel frit pastes which set within 2–3 minutes or less show a linear trend apparently contrasted by resin content in the mixed paste. Increase in the filler content or reduction in the resin content results in strengths attaining that of "Adaptic".

(j) Water pickup.—Water pickup in the various products has no obvious relationship to flexure strength (Tables XVII and XVIII). However, no products containing the novel frits absorbing as much as 0.090 grams of water per ml of mixed paste had flexure strengths in excess of 765 kg/cm² (upper limit of strength rank IV). Also, no novel products which absorbed more than 0.057 grams of water per ml of mixed paste had flexure strengths in excess of 823 kg/cm² (upper limit of strength rank III).

The novel commercial grain and frit filled products do not exceed 981 kg/cm² (upper limit of strength) rank II) if they contain more than 0.025 grams of water per ml of paste. All strength rank categories except V (upper limit 611 kg/cm₂) are represented by the novel products absorbing less than 0.025 grams of water per ml of paste.

Examination of the water pickup tables (Tables XVII and XVIII) reveals that high filler contents or low vol. % resin in the mixed paste tend to have lower water absorption. However, as with flexure strength, no clear relationship was found between water pickup and filler content.

(k) Finishability.—"Adaptic" restorations finished with a zirconium silicate disc preceded by a Shofu point are rough. Quartz filler grain on finished "Adaptic" surfaces have minute triangular pits. This feature is diagnostic of impact grinding. Detailed SEM examination reveals that filler is degraded by impact at its margin. After peripheral degradation the relict quartz core is released or pushed out.

X-ray opacifying glass beads in "Prestige" are even more susceptible to degradation by impact. SEM photographs show the progressive degradation of this glass filler. Impact degradation is evident initially at the margins and progresses until the remaining grain is released or plucked out.

Optical microscopic examination of polished glass-bead filled BIS-GMA systems commonly shows peripheral degradation of the glass beads by impact. Glass bead and other hard, rigid filler grains under some circumstances appear to be liberated by transmission of impact shocks to the filler grain boundaries.

Figure 4:
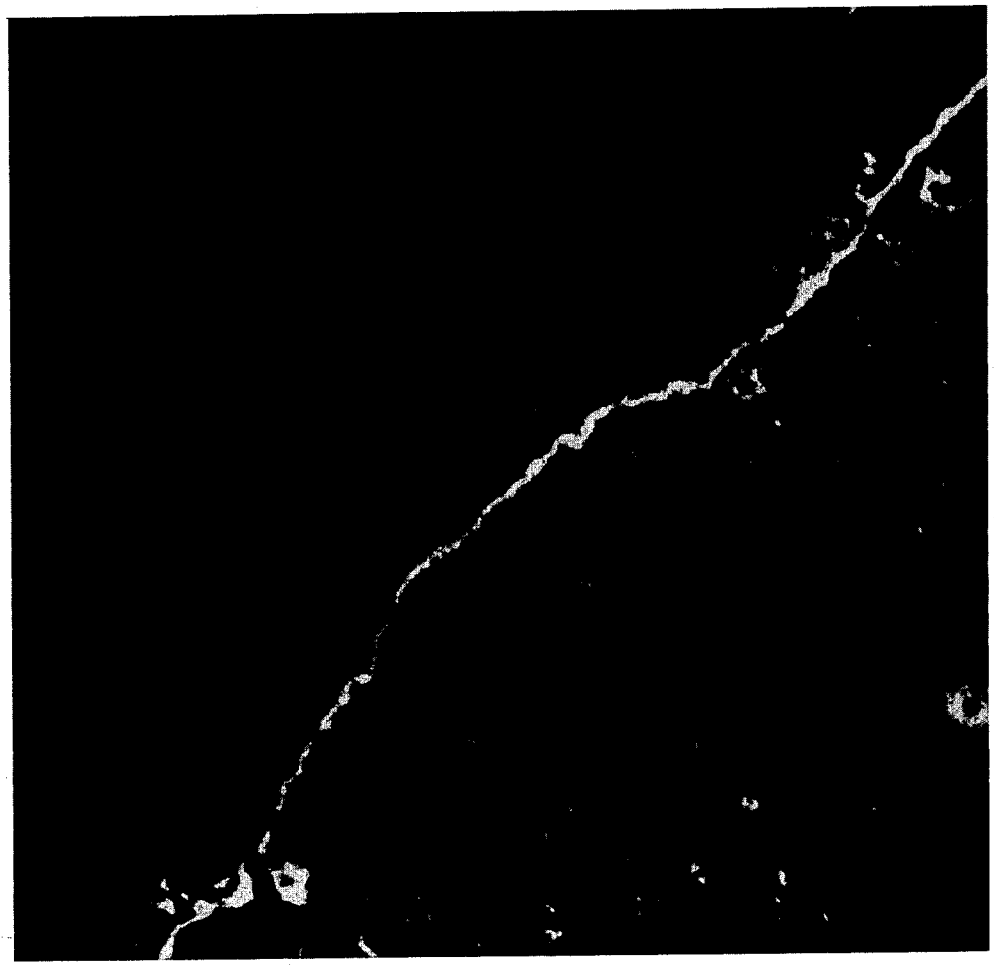
FIG. 4 shows microscopic examination of tooth restored using the novel filler of this invention.

Finishes developed on restorations of products containing the novel frit grain usually appear the same as that on the tooth under stereoscopic and ultrapack optical microscopic and SEM examination (Table XIX). Scratches developed by zirconium silicate discs and Shofu points are commonly more evident in the adjacent tooth than the novel frit product restorations. See FIG. 4.

Figure 5:
FIG. 5 shows microscopic examination of heavily finished tooth restoration made with novel filler, mix #86.

When heavily finished with a large amount of impact, restorations made from products containing the novel frit are not torn up more than tooth. Tooth and novel frit containing restoration surfaces respond approximately the same to deep gouging and scratching. See FIG. 5. Deep gouges and scratches transect both novel frit grain and resin matrix without deflection.

Heavily finished restorations do not exhibit the impact fragmentation exhibited by quartz or glass-bead filler grain. Tooth crystals and novel frit grain appear to be disrupted to about the same degree.

Finishing heavily usually forms a trough filled with detritus in the ground surface at the restoration-tooth boundary.

Figure 6:
FIG. 6 shows microscopic examination of gently finished tooth restoration using novel filler product, mix #96.

When finishing is sufficiently gentle and low in impact, tooth resin interfacial troughs are not generated. Instead smooth, complete marginal contact is exhibited on the polished surface of the restoration and the tooth contact. See FIG. 6.

In all observed finishing procedures even large experimental frit filler particles are well retained. Most of the pits and holes in the finished experimental frit-containing restoration surface are inherent in the resin. Commonly, scratches and grooves in the adjacent finished tooth are deeper than in the novel frit-containing restoration.

When polished, novel frit cleaves in a smooth spall-like fashion. High magnification SEM fracturographs show that the novel frit grain exhibits a layered spalling.

(1) X-ray opacification.—Acceptable radiopacity and translucency can be achieved utilizing products which have in the mixed paste 58 vol. % novel frit (mix #96). These frits contain about 22 mass % $ZrO_2$. The x-ray opacification in all novel frit products greatly exceeds that of the non-x-ray opacifying "Adaptic" which contains about 61 vol. % quartz filler in the mixed paste.

The novel frits yielding products of marginal translucency (0.55) and containing higher amounts of $ZrO_2$, about 28 mass %, and less filler, about 52 vol. % in the mixed paste, have a slightly more satisafactory x-ray opacification. A high x-ray opacification can be achieved in restorations with about 37.5 vol. % in the mixed paste of tin-containing experimental frit. This novel frit contains, in mass percent, about 12% Sn and about 22% $ZrO_2$ (mix #116).

Alternatives and Variations: Resin composites prepared utilizing filler frits prepared by the gel route are capable of considerable variation. Reduced setting contraction and thermal expansion can be obtained by increase in the filler content. Increase in filler content can be accomplished by reducing the proportion of extreme fines produced to date in the frits. Elimination of unnecessary fine frit particles will reduce the build-up by filler of resin paste viscosity. This will allow the introduction of greater amounts of filler.

Optimal particle size distributions can be obtained by air classification procedures. The optimal particle size distributions are those with nominal diameters best for strength but not fine enough to induce excessive paste viscosity. Particles coarser than 200-mesh must be avoided. Paste preparation should be done by introducing the coarser frit particles first and then the finer.

For a given frit composition, refractive index and density are a function of one another. Therefore, liquid gravity separations can be used to control the refractive index of the frit product. Both translucency and strength can be improved by eliminating the low refractive index component. Opacification can be adjusted by allowing a greater or less contribution by the higher index and denser frits. As has been demonstrated, other commercial fillers, e.g. glass beads, quartz, and fused silica fiber, can be added to adjust strength and translucency.

Improvement of gelling procedures directed toward removing inhomogeneities in the gel starting product are possible. The precise micro-environment in which the gelling takes place, solvent immiscibility, the rate of cure, etc., will result in gel inhomogeneity. Making the gelling environment more consistent from one site to another should result in cured gels with a more uniform microporous structure.

Greater uniformity in the microporosity of the cured gelled feed for calcination should result in a final frit product with a more precisely targeted refractive index. Cured gel feed with a uniform microporosity, upon a given heat treatment, should attain the same density and, therefore, refractive index throughout.

Rapid firing electric belt kilns can be utilized to control precisely calcination procedures. As mentioned, an electric belt kiln was utilized in this study. Cured and defumed gelled frit were spread as thin layers over thin high density alumina plates which were then placed on a belt and passed through the electric kiln.

It is possible to optimize gel prepared frit composition to obtain fillers with low thermal expansion and high x-ray opacification. Two of the elements which have K absorption edges which closely match the K emissions of the tungsten radiation used for dental x-rays are tantalum and hafnium. Both of these elements could be substituted for zirconium used in the preferred embodiment. It is well known that hafnium is a chemical twin of zirconium and would present few problems in its introduction into gel prepared frits. In fact, hafnium has greater x-ray opacification than zirconium. Therefore, the substitution of hafnium for zirconium should permit greater flexibility in determining the optimum filler to resin ratio without sacrificing x-ray opacity qualities.

Gel preparation of frits allows the introduction of high x-ray opacifying ingredients and those which are known to have lower thermal expansion, e.g., zirconium, in a way so as not to result in unsatisfactory frit optical properties. Frit microporosity or density is adjusted to counter balance the raising of its refractive index by the constituents which increase x-ray opacity and reduce thermal expansion.

Other methods of heat treatment of the gelled and pre-calcined or fumed frit may be possible. Flame spray techniques may also prove useful in this regard. Pre-calcined frits are being flame-sprayed in oxygen acetylene flames and collected on water filters. Subsequent to settling out they are washed, filtered out and dried.

Flame-spray techniques may result in the production of frits with a high degree of densification without excessive crystallization. Thin high density skins developed on the surface of particles by flame-spray techniques may result in lower water pickup in the filler grain and possibly reduced solubility. Flame-spray techniques may be used to produce high sphericity particles with a smoother surface and less hydraulic drag at the resin-filler interface. This may result in frits which allow for the preparation of resin pastes with higher filler contents.

The frits of this invention can be made to carry conventional pigments. For example, carbon black can be used to introduce gray shades. This has been done by using about half the normal amount of nitric acid and using zirconium acetate to introduce zirconium oxide into the gel. A grayish core remains in the fritted grain which contains graphitized carbon. This carbon is not in contact with the surrounding resin, and, therefore, should not create the color instability in the resin matrix commonly attributed to carbon black. Certain prior art pigments are too reactive with the resin system and can cause deterioration in the glass melting operation.

It is obvious that color and opacifier can be carried by the gel-prepared frits. The novel frit preparation temperatures are lower than those normally encountered in glass melting procedures. Therefore, pigments can be incorporated which would be unstable at the temperature required to melt glass. Also, pigments may be carried inside the novel frits out of contact with the resin matrix so as not to contribute to color instability, poor shelf life, or setting problems.

The above description relates to typical embodiments of the invention and some of its equivalents. However, additional alternative formulations and procedures and other modifications are possible within the scope of the invention. For example, these novel frits appear particularly susceptible to improvement by the elimination of the finest components of the particle size distribution. This would allow introduction of more filler into the resin paste system. Then reduced thermal expansion and setting contraction and increased strength, higher elastic moduli, and increased microhardness could be expected. Extrapolated curves indicate that the introduction of 6 vol. % more formulations would result in the strength, elastic moduli, and microhardness of Adaptic. Also, experimental frits are susceptible to improvement by the better control of gelling and heat treatments involved in their production. Frits with more consistent microporosity and density could thus be produced. The close association of frit density with frit refractive index permits the utilization of gravity separation techniques to obtain frits with refractive indices closely matched to that of the resin matrix. Therefore, the subject matter of the invention is to be limited only by the following claims and their equivalents.

What is claimed is:

1. In a dental resin composite comprising a resin and a filler material the improvement which comprises the replacement of at least a portion, if not all, of said filler material with a non-toxic, substantially uniform internally microporous glassy filler having a median refractive index between about 1.51 and about 1.64 and a density between about 2.37 and about 3.15 grams per cubic centimeter, said microporous glassy filler comprising a gelled, calcined sol comprised of refractory inorganic oxides including silica and alumina, and at least one non-toxic x-ray opacifying oxide selected from the group consisting of zirconium, hafnium, tantalum and tin oxides.

2. A composite as claimed in claim 1 wherein said microporous glassy filler comprises about 27 to 57 percent by weight silicon dioxide.

3. A composite as claimed in claim 1 wherein said microporous glassy filler comprises about 13 to about 60 percent by weight aluminum oxide.

4. A composite as claimed in claim 1 wherein said x-ray opacifying oxide is zirconium oxide comprising from about 18 to about 36 percent by weight of said microporous glassy filler.

5. A composite as claimed in claim 1 wherein said microporous glassy filler further comprises a fluxing agent in an amount less than about 0.2 percent by weight.

6. A composite as claimed in claim 6 wherein said fluxing agent is selected from the group consisting of boric anhydride, phosphorous pentoxide, lithium oxide, and sodium oxide.

7. A composite as claimed in claim 1 wherein said sol further comprises a coloring pigment.

8. A composite as claimed in claim 1 wherein said coloring pigment comprises carbon black.

9. A composite as claimed in claim 1 wherein said resin comprises about 50 to about 80 percent 2,3-bis 4-(3-methacryloxy-2-hydroxypropoxy)phenylpropane, and about 50 to about 20 percent triethylene glycol-dimethacrylate.

10. A composite as claimed in claim 1 wherein said resin includes a catalyst selected from the group consisting of benzoyl peroxide or dihydroxy-ethyl p-toluidine.

11. A composite as claimed in claim 1 wherein said resin includes 2,6-di-t-butyl-p-methyl phenol as a stabilizer.

12. A composite as claimed in claim 1 wherein said x-ray opacifying oxide is tin oxide.

13. A composite as claimed in claim 1 wherein said microporous glassy filler has a median refractive index between about 1.55 and about 1.57.

14. A composite as claimed in claim 1 wherein said internally microporous glassy filler comprises:
(a) about 27 to about 57 percent by weight silicon dioxide;
(b) about 13 to about 60 percent by weight aluminum oxide; and
(c) about 10 to about 36 percent by weight of said non-toxic x-ray opacifying oxide.

15. A composite as claimed in claim 1 wherein the crystallinity of said filler is less than about 5 percent by volume.

* * * * *

UNITED STATES PATENT OFFICE
CERTIFICATE OF CORRECTION

Patent No. 4,217,264  Dated August 12, 1980

Inventor(s) MABIE ET AL.

It is certified that error appears in the above-identified patent and that said Letters Patent are hereby corrected as shown below:

Col. 3, line 25 "give" should be —given—.

Col. 8, line 62, "Composites (unpublished).""  should be —Composites" (unpublished).—

Table II, "XIX  26  —  —  50  135  —  —  1  1  15  280  200" should be
—XIX  26  —  —  50  135  —  —  1  1  —  15  280  200—.

Table III, line XIV "46.055" should be moved over 1 space to the left.

Table IV, line II-2 "910" should be —920—; line VII-1 "1 hr." should be —3 hr.—; line VIII-2 "550-550" should be —550-650—; XXVI "1 1/2" should be —3 1/2—; XXXI "1010-1060" should be —1020-1060—; and XXX-1 "910-1000" should be —930-1000—. Footnote b "205" should be —20T— and "CAR" should be —CAE—.

Table V under the description of Density gm/cc, "h" should be "n" in both cols. 18 and 19; line II- 1 "1.530-1.500" should be —1.530-1.580—; line XII "1.648" should be —1.548—; line XIV-3 "1.639" should be —1.638—; line XVIII "1.530-1.639" should be —1.530-1.630—; line XXIII-1 "1.594-1.650  1.582" should be —1.534-1.-1.650  1.592—; and the last line XXXIII "1.576-1.606" should be —1.526-1.606—.

Table VI line F under "760°C" should be —1 hr.—.

Col. 22, line 53, "ater" should be —after—.

Table IX No. 15 "K" should be —H—; No. 96, "79.1" should be —75.1—; No. 107, "71.1" should be —73.1—; No. 108, "64.1" should be —66.1—; No. 109, "6" should be —8—; No. 110, "66.6" should be —68.5—; and No. 111, "69.4" should be —69.6—.

UNITED STATES PATENT OFFICE

CERTIFICATE OF CORRECTION

Patent No. 4,217,264  Dated August 12, 1980

Inventor(s) MABIE ET AL.

It is certified that error appears in the above-identified patent and that said Letters Patent are hereby corrected as shown below:

Table X, line "[XVII-1]  —  —  —" should be —[XVII-1]  —  —  50.6—.

Table XI, Filler "XI    88" should be --XI    83—.

Table XVI and the third section, line "II-3  11  6  47.0  46.8-47.2  110-132  0.0841  40-45  2 1/2  724  ±131  124  —" should all be shifted over 1 column to the right; at XXVII-2 in approximately col. 41, "45 - 2-1/3  2-1/2    710    —" should be —45-50(g)    2-1/2    710—.

Col. 48, bottom of the page "TABLE" should be --TABLE XVIII--; cols. 49 & 50, at the top of the page, "TABLE-continued" should be --TABLE XVIII-continued--; cols. 51 and 52, at the top of the page, "TABLE-continued" should be --TABLE XVIII-continued--. In the third, fourth and fifth column headings to Table XVIII, appearing at cols. 48, 49-50 and 51-52, "m $10^{-3}$", "m $10^{-2}$" and "m $10^{-2}$" should be --x $10^{-2}$--, --x $10^{-2}$-- and --x $10^{-2}$--, respectively.

Col. 57, line 68, "See FIG. 10." should be deleted.

Col. 62, line 13, Claim 2, "said microporous glassy filler comprises about 27 to 57" should be --said internally microporous glassy filler comprises about 27 to about 57--.

UNITED STATES PATENT OFFICE
CERTIFICATE OF CORRECTION

Patent No. 4,217,264             Dated August 12, 1980

Inventor(s)  MABIE ET AL.

It is certified that error appears in the above-identified patent and that said Letters Patent are hereby corrected as shown below:

Column 62, line 15, Claim 3, "said microporous glassy filler" should be -- said internally microporous glassy filler --.

Signed and Sealed this

Twelfth Day of May 1981

[SEAL]

Attest:

RENE D. TEGTMEYER

Attesting Officer      Acting Commissioner of Patents and Trademarks